US009601393B2

(12) United States Patent
Lee et al.

(10) Patent No.: US 9,601,393 B2
(45) Date of Patent: Mar. 21, 2017

(54) SELECTING ONE OR MORE PARAMETERS FOR INSPECTION OF A WAFER

(75) Inventors: Chris Lee, Fremont, CA (US); Lisheng Gao, Morgan Hill, CA (US); Tao Luo, Fremont, CA (US); Kenong Wu, Davis, CA (US); Tommaso Torelli, Berkeley, CA (US); Michael J. Van Riet, Sunnyvale, CA (US); Brian Duffy, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 555 days.

(21) Appl. No.: 13/148,473

(22) PCT Filed: Feb. 5, 2010

(86) PCT No.: PCT/US2010/023396
§ 371 (c)(1),
(2), (4) Date: Aug. 8, 2011

(87) PCT Pub. No.: WO2010/091307
PCT Pub. Date: Aug. 12, 2010

(65) Prior Publication Data
US 2011/0320149 A1 Dec. 29, 2011

Related U.S. Application Data

(60) Provisional application No. 61/150,549, filed on Feb. 6, 2009.

(51) Int. Cl.
*G01N 21/95* (2006.01)
*H01L 21/66* (2006.01)

(52) U.S. Cl.
CPC .......... *H01L 22/20* (2013.01); *G01N 21/9501* (2013.01); *H01L 22/12* (2013.01); *H01L 2924/0002* (2013.01)

(58) Field of Classification Search
CPC .................................. H01L 22/00; H01L 22/12
USPC ............................................................ 702/83
See application file for complete search history.

(56) References Cited

U.S. PATENT DOCUMENTS

| 6,999,614 | B1 |  | 2/2006 | Bakker et al. |
| 7,142,992 | B1 | * | 11/2006 | Huet et al. ...................... 702/58 |
| 7,269,816 | B2 |  | 9/2007 | Bevis |
| 7,570,797 | B1 |  | 8/2009 | Wang et al. |
| 8,135,204 | B1 | * | 3/2012 | Chen et al. .................. 382/141 |
| 2004/0095573 | A1 |  | 5/2004 | Tsai et al. |

(Continued)

FOREIGN PATENT DOCUMENTS

| JP | 2001-168160 | 6/2001 |
| JP | 2004-294358 | 10/2004 |

(Continued)

OTHER PUBLICATIONS

Sang Chong, Accelerated 65nm Yield Ramp through Optimization of Inspection on Process-Design Sensitive Test Chips, 2007, pp. 69-73.*

(Continued)

*Primary Examiner* — Michael Nghiem
*Assistant Examiner* — Peter Ngo
(74) *Attorney, Agent, or Firm* — Ann Marie Mewherter

(57) ABSTRACT

Computer-implemented methods, computer-readable media, and systems for selecting one or more parameters for inspection of a wafer are provided.

69 Claims, 2 Drawing Sheets

(56) References Cited

U.S. PATENT DOCUMENTS

| | | | |
|---|---|---|---|
| 2004/0228515 A1* | 11/2004 | Okabe et al. | 382/145 |
| 2005/0004774 A1* | 1/2005 | Volk et al. | 702/108 |
| 2005/0092899 A1 | 5/2005 | Wolf et al. | |
| 2005/0160394 A1 | 7/2005 | Bevis | |
| 2006/0082763 A1 | 4/2006 | Teh et al. | |
| 2006/0159330 A1* | 7/2006 | Sakai et al. | 382/141 |
| 2006/0287751 A1 | 12/2006 | Dishner et al. | |
| 2007/0121106 A1 | 5/2007 | Shibata et al. | |
| 2007/0156379 A1 | 7/2007 | Kulkarni et al. | |
| 2007/0288219 A1* | 12/2007 | Zafar et al. | 703/14 |
| 2008/0081385 A1* | 4/2008 | Marella et al. | 438/14 |
| 2008/0094639 A1* | 4/2008 | Widmann et al. | 356/601 |
| 2008/0163140 A1* | 7/2008 | Fouquet et al. | 716/4 |
| 2008/0250384 A1 | 10/2008 | Duffy et al. | |
| 2008/0279444 A1* | 11/2008 | Fischer et al. | 382/145 |
| 2009/0080759 A1 | 3/2009 | Bhaskar et al. | |

FOREIGN PATENT DOCUMENTS

| | | |
|---|---|---|
| JP | 2005-017159 | 1/2005 |
| KR | 10-2006-0128277 | 12/2006 |
| KR | 10-0761851 | 9/2007 |
| KR | 10-2008-0073281 | 8/2008 |

OTHER PUBLICATIONS

International Search Report and Written Opinion for PCT/US2010/023396 mailed Aug. 24, 2010.
International Preliminary Report on Patentability for PCT/US2010/023396 mailed Aug. 18, 2011.
Notice of Grounds for Rejection for Japanese Patent Application No. 2011-549298 mailed Jan. 28, 2014.

* cited by examiner

SELECTING ONE OR MORE PARAMETERS FOR INSPECTION OF A WAFER

PRIORITY CLAIM

This application is a National Stage application of International Application No. PCT/US10/23396 filed Feb. 5, 2010, which claims priority to U.S. Provisional Application No. 61/150,549 entitled "Computer-Implemented Methods, Computer-Readable Media, and Systems for Selecting One or More Parameters for Inspection of a Wafer," filed Feb. 6, 2009, which is incorporated by reference as if fully set forth herein.

BACKGROUND OF THE INVENTION

1. Field of the Invention

This invention generally relates to selecting one or more parameters for inspection of a wafer. Certain embodiments relate to selecting one or more parameters for a multi-test inspection of a wafer given one or more optical modes.

2. Description of the Related Art

The following description and examples are not admitted be prior art by virtue of their inclusion in this section.

Inspection processes are used at various steps during a semiconductor manufacturing process to detect defects on wafers. Inspection for many different types of defects has become more important recently. In some instances, a system that is configured to detect different types of defects may have adjustable output acquisition and sensitivity (or defect detection) parameters such that different parameters can be used to detect different defects or avoid sources of unwanted (nuisance) events. For instance, the spot or pixel size, wavelength, aperture, focus offset, polarization, or angles of collection may be different for an inspection process used to detect particulate defects than for an inspection process used to detect scratches.

Although an inspection system that has adjustable output acquisition and sensitivity parameters presents significant advantages to a semiconductor device manufacturer, these inspection systems are essentially useless if incorrect output acquisition (e.g., data, signal, and/or image acquisition) and/or sensitivity parameters are used for an inspection process. For example, incorrect or non-optimized output acquisition parameters may produce such high levels of noise that no defects of interest (DOI) can be detected in the generated output. in addition, since the defects, process conditions, and noise on a wafer may vary dramatically, the best output acquisition and sensitivity parameters for detecting the defects on a particular wafer may be difficult, if not impossible, to predict. Therefore, although using the correct output acquisition and sensitivity parameters will have a dramatic effect on the results of inspection, it is conceivable that many inspection processes are currently being performed with incorrect or non-optimized output acquisition and/or sensitivity parameters.

The task of setting up an inspection process for a particular wafer and a particular DOI may be extremely difficult for a user particularly when an inspection system has a relatively large number of adjustable output acquisition settings and sensitivity parameters. However, most inspection processes are currently set up using a large number of manual processes (e.g., manually selecting the output acquisition parameters, manually analyzing the inspection results, etc.). As such, setting up the inspection process may take a relatively long time. Furthermore, depending on the types of wafers that will be inspected with the inspection system, a different inspection process may need to be set up for each different type of wafer. Obviously, therefore, setting up the inspection processes for all of the different wafers that are to be inspected may take a prohibitively long time.

Furthermore, it may be desirable to perform inspection of wafers using a multi-pass or multi-scan inspection process. Different parameters for inspection may be used for each pass or scan. One currently used method for multi-pass inspection setup is to set up the multiple scans individually. While parts of the setup may be common among scans such as light level training and Fourier filter training, often the parameters for each scan are independent of the other scans' parameters and must be optimized separately. The major, time consuming effort is in two areas, optics selection and defect detection algorithm parameter optimization.

To perform optics selection in the above-described setup method, the user selects a combination of optical modes based on the signal-to-noise ratio (S/N) of a selected set of defects, which includes both DOI and nuisance. The S/N for each defect is collected from individual optical modes and is listed in a table. The user then analyzes the table contents in order to pick the best optical modes, typically those with high S/N for DOI and low S/N for nuisance.

For the algorithm parameter optimization step, the user tunes the detection algorithm parameters for each scan to maximize the DOI capture and minimize nuisance/noise capture on the inspection system or with the assistance of optimization tools a sensitivity tuner) after the user classifies samples of detected detects through optical or scanning electron microscope (SEM) review. The result is the optimized set of algorithm parameters for each individual scan. If the user needs to coordinate the scans for further optimization, such optimization can involve intensive data analysis. Sometimes engineering efforts, such as software development, are necessary for such optimization due to its complexity or sheer number of combinations under consideration.

The method described above has a number of disadvantages. For example, the method described above for multi-pass inspection setup is substantially labor intensive. Given the flexibility and complexity that most advanced inspection systems offer, there are typically substantially large numbers of optical mode combinations one can explore. Often, if a single inspection scan cannot provide the required DOI sensitivity and/or nuisance capture rate, the user cannot afford the time to consider combinations of optical modes and perform multiple passes of sensitivity parameter tuning. In addition, simply combining the results from individually optimized scans may not lead to optimal inspection results. To achieve the best inspection results, multiple scans need to work together in a complementary fashion to detect as many DOI and suppress as many nuisances as possible. Due to limited time and capability of optimization tool sets, these multi-pass options cannot be adequately explored often resulting in sub-optimal inspection outcomes.

Accordingly, it would be advantageous to develop methods and/or systems for selecting one or more parameters for inspection of a wafer that are less labor intensive, quicker, and less tedious than previously used methods and can be used to select one or more parameters for a multi-pass or multi-scan inspection that are more suitable, or even optimal, for the inspection than parameters of multi-pass or multi-scan inspections selected using the method described above.

SUMMARY OF THE INVENTION

The following description of various embodiments is not to be construed in any way as limiting the subject matter of the appended claims.

One embodiment relates to a computer-implemented method for selecting one or more parameters for inspection of a wafer. The method includes acquiring output of an inspection system for defects on the wafer using individual optical modes of the inspection system. The defects include defects of interest (DOI) and nuisance defects. The method also includes determining capture rates of the DOI and capture rates of the nuisance defects for the individual optical modes and for one or more combinations of the individual optical modes using the output. In addition, the method includes determining scores for the individual optical modes and the one or more combinations as a function of the capture rates of the DOI and the capture rates of the nuisance defects. The method further includes selecting one of the individual optical modes or one of the one or more combinations for the inspection of the wafer based on the scores.

The method described above may be performed as described further herein. In addition, the method described above may include any other step(s) of any other method(s) described herein. Furthermore, the method described above may be performed by any of the systems described herein.

Another embodiment relates to a computer-readable medium that includes program instructions executable on a computer system for performing a computer-implemented method for selecting one or more parameters for inspection of a wafer. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to select one or more parameters for inspection of a wafer. The system includes an inspection system configured to acquire output for defects on the wafer using individual optical modes of the inspection system. The defects include DOI and nuisance defects. The system also includes a computer system configured to determine capture rates of the DOI and capture rates of the nuisance defects for the individual optical modes and for one or more combinations of the individual optical modes using the output. The computer system is also configured to determine scores for the individual optical modes and the one or more combinations as a function of the capture rates of the DOI and the capture rates of the nuisance defects. In addition, the computer system is configured to select one of the individual optical modes or one of the one or more combinations for the inspection of the wafer based on the scores. The system may be further configured as described herein.

A further embodiment relates to another computer-implemented method for selecting one or more parameters for inspection of a wafer. This method includes performing one or more inspection tests on a wafer to determine locations of DOI and nuisance defects on the wafer. The method also includes acquiring output of an inspection system at the locations on the wafer using individual optical modes of the inspection system. In addition, the method includes selecting one or more parameters for the inspection of the wafer based on the output acquired at the locations on the wafer using the individual optical modes.

Each of the steps of the method described above may be performed as described further herein. In addition, the embodiment of the method described above may include any other step(s) of any other method(s) described herein. Furthermore, the embodiment of the method described above may be performed by any of the systems described herein.

BRIEF DESCRIPTION OF THE DRAWINGS

Other objects and advantages of the invention will become apparent upon reading the following detailed description and upon reference to the accompanying drawings in which.

Figure 1:
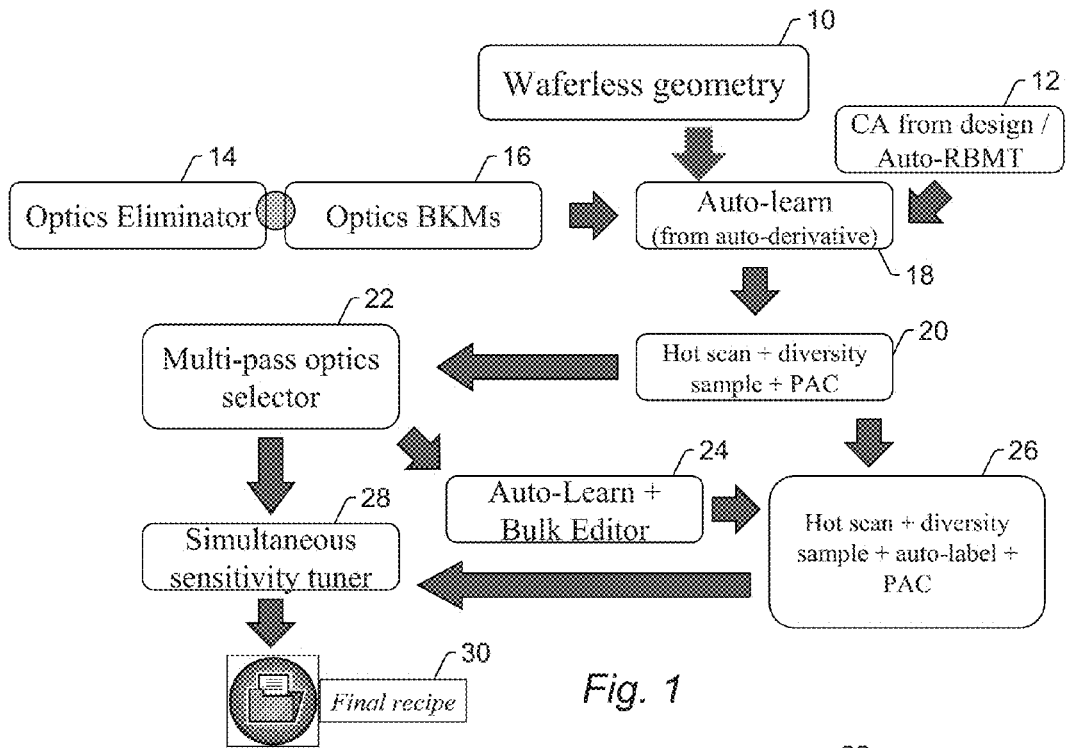
FIGS. 1 and 2 are flow charts illustrating different embodiments of a computer-implemented method for selecting one or more parameters for inspection of a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of scale of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to a computer-implemented method for selecting one or more parameters for inspection of a wafer. The embodiments described herein may be used for setting up wafer inspection processes that include multiple scans (or multiple passes), which are performed with one or more different optical parameters and/or one or more different defect detection parameters. For example, the embodiments described herein my be used to set up a recipe for wafer inspection involving scans performed with multiple optical states on the same area of the wafer with optimum sensitivity and nuisance rate. A "recipe" is generally defined as a set of instructions that can be used by a system such as an inspection system to perform a process such an inspection process.

Multiple scans may be used in an inspection process since any one single scan may be limited in achievable sensitivity and nuisance suppression. For example, it is increasingly necessary to perform multiple inspections of the same area of a wafer to provide the end user with the overall signal-to-noise ratio (S/N) that they desire. In addition, some defects show up differently using different optical modes. In this manner, multi-scan or multi-pass inspection may include inspecting the same area on a wafer multiple times with different optical modes and/or inspection parameters. Each inspection catches one or more types of defects, but not all types. Only with all these inspections, all types of defects can be captured. These inspections are complementary in order to capture all types of defects. In this manner, such multi-scan or multi-pass inspection may be commonly referred to as "complementary inspection." As such, multiple scans performed in an inspection process may complement one another such that the output acquired from all of the scans can be used to reduce nuisance detection while maintaining or even increasing defect of interest (DOI) detection. Therefore, by using multiple passes to inspect a wafer, the DOI to nuisance capture rate ratio can be optimized, provided that the multiple passes are performed with suitable optical modes and with appropriate defect detection parameters. Setting up complementary inspection is one use case for which the embodiments described herein are particularly suitable and useful.

The embodiments described herein may be used to improve the set up of multi-pass inspection by providing an optimization method to manually or automatically select single or multiple optical modes, and if multiple optical modes are selected, to manually or automatically perform tuning of the sensitivity (or defect detection) parameters of all scans simultaneously to achieve the best inspection results. In this manner, the embodiments described herein for multi-scan inspection set up focus on the optimization of DOI sensitivity and nuisance suppression of multiple scans using both optical parameter selection and defect detection parameter tuning approaches.

The method includes an optical parameter selection stage in which an individual optical mode or a combination of individual optical modes is selected for the inspection of the wafer. For example, the method includes acquiring output of an inspection system for defects on the wafer using individual optical modes of the inspection system. The output that is acquired and used in the methods described herein may include any output of the inspection system (e.g., output such as data, signals, image data, etc, generated by one or more detectors or one or more detection channels of the inspection system). As used herein, a "mode" or an "optical mode" generally refers to a single optical combination that includes a number of optical components including, but not limited to, a wavelength filter, one or more polarization filters, an aperture, and an objective set. In this manner, an optical mode may be defined by the parameters of various optical components of the inspection system that are or can be used in combination to scan the wafer thereby acquiring output for the wafer. Therefore, selecting an optical mode or optical mode combination as described herein effectively selects one or more (optical) parameters for the inspection of the wafer.

The methods described herein are not limited in the types of inspection systems for which one or more parameters can be selected. For example, in one embodiment, the inspection system includes a dark field (DF) inspection system. The DF inspection system may be configured as described further herein. In other embodiments, the inspection system includes a bright field (BF) inspection system. The BF inspection system may have any suitable configuration known in the art. The inspection system may also be configured for DF and BF inspection. In addition, the inspection system may be configured for inspection of patterned wafers and/or unpatterned wafers.

In one embodiment, acquiring the output includes scanning the defects on the wafer using the inspection system. For example, during the optical parameter selection stage, a set of defects on the wafer may be scanned using a base inspection system configuration and a number of optical modes. Each defect is scanned in each mode. In addition, acquiring the output may include acquiring output for each defect in a variety of optical modes that are selected by the user. The base inspection system configuration may depend on the application (e.g., the type of inspection that will be performed), one or more characteristics of the wafer, one or more characteristics of the defects, user knowledge, etc., or some combination thereof. For example, the base inspection system configuration may be a configuration that is known to be capable of detecting DOI. Acquiring the output by scanning the defects may include scanning substantially the entire wafer or scanning only areas of the wafer in which the defects are located.

The set of defects for which output is acquired in this step may include a predetermined set of defects that have been detected on the wafer using output previously acquired for the wafer. For example, the predetermined set of defects may have been detected by scanning the wafer using a well-characterized scan. In addition, the method may include defining a set of inspection tests for the same sample plan for the "initial inspection." After the tests have been defined, they may be executed.

In this manner, the one or more parameters for the inspection of the wafer may be selected in a deterministic manner. For example, the embodiments described herein are deterministic in the sense that they use cumulative learning about known locations of DOI and nuisance regions on a wafer. Therefore, the embodiments described herein enable a deterministic defect-by-defect analysis of the efficacy of a given inspection to detect that defect. In addition, the embodiments described herein introduce the deterministic (versus probabilistic) application of learning from multiple inspection test passes for the purpose of creating a defect and nuisance "reference set" that will be used to test the efficacy of all candidate inspection schemes (single pass or a combination of passes). As such, the embodiments described herein may be used for "deterministic" multi-pass inspection recipe setup. In contrast, conventional means of inspection setup require that the user operate on disparate groups of defects that may or may not overlap from inspection condition to inspection condition. This makes the overall process risky in that one is dependent on speculation as to the statistical behavior of defect populations.

It may be useful to introduce and define a number of new terms to describe deterministic inspection recipe setup thereby formalizing the language of deterministic multi-pass setup. For example, normal defect detection terms include defect; DOI; defective pixel; nuisance; multi-pass setup; multi-pass inspection; care areas; don't care areas; rule based binning (RBB): rule based inspection (RBI); hot inspection; S/N (or SNR); capture rate (or cap rate); and sample plan. In contrast, new terms for deterministic multi-pass setup include: data synthesis; defect instance; pseudo-defect; pseudo-nuisance; nuisance of interest; pixels of interest; pixels of no interest; injected defect; simulated defect; points-of-interest; points-of-no-interest; regions of interest; regions of no interest; iso-noise; iso-noise regions; cost function; detectability; detectability margin; suppress-ability; and suppress-ability margin.

In one such example, the term "DOI" typically refers to a "defect type of interest," technically a class of defects. To be clear, we introduce the term "defect instance"—a single physical defect that is of interest to the end user. In other words, a "defect instance" may be defined as one specific physical defect that just happens to be a member of a class of defects. This term helps separate the physical existence of a defect we want to detect versus a defect that we actually detected in a given inspection. For a given wafer, "defect instances of interest" are an absolute—the end user wants to know about these locations that are known to be present on a wafer irrespective of the means of detecting them and irrespective of whether a given inspection detects them. A practical means of identifying the "defect instances of interest" is the logical "OR" of multiple inspections (typically with scanning electron microscope (SEM) review) to identify "defects" and "nuisance."

The term "injected defect" can be generally defined as a location that is artificially declared to be defective. For example, given a set of conditions, one can declare that this location should be a defective location. Such locations can be used to test algorithms and to test coverage evaluation methods. An injected defect may be artificially created by modifying a structure or inserting defects to see what they look like to the inspection system and to determine if they would be detected. An injected defect may include any type of defect such as a pattern defect, a relatively high aspect ratio defect, DRAM structures, etc.

A "point-of-interest" can be generally defined as a point on a wafer that is of interest. Similarly, a "point-of-no-interest" can be generally defined as a point on a wafer that is of no interest. The terms "iso-noise" and "iso-noise region" generally refer to results of image segmentation in which an image is separated into sets of pixels that behave similarly in terms of noise (e.g., have similar noise characteristics). A "cost function" can be generally defined with respect to deterministic inspection recipe set up as a function that can be used to determine the best coverage with the minimum number of modes. A "detectability margin" can be generally defined as the separation between defects and noise. One example of a measure of the detectability is the MDAT gray level (GL), which is described further herein. A "suppress-ability margin" can be generally defined as the noise floor area.

In one embodiment, the method includes identifying the defects on the wafer prior to acquiring the output by performing one or more inspection tests on the wafer. The one or more inspection tests may be performed as described further herein (e.g., using a base recipe and/or a base inspection configuration). In one such embodiment, the one or more inspection tests do not include the individual optical mode or the combination of the individual optical modes ultimately selected for the inspection. For example, a consequence (and benefit) of the methodology described herein is that the inspection conditions of the final inspection recipe need not be a subset of the conditions used in the learning passes (i.e., the one or more inspection tests). In another such embodiment, the one or more inspection tests are performed using an additional inspection system having an inspection platform different than an inspection platform of the inspection system. For example, the learning may occur on a different inspection platform from the one the final recipe is being developed for as long as the various inspection platforms have sufficient pixel level coordinate accuracy versus design criteria.

For multi-pass inspections, there are currently numerous conventions for leveraging the advantages of combining multiple inspection passes that can also be used to identify the DOI and/or nuisance defects on the wafer during the learning phase. For example, in one embodiment, the method includes identifying the DOI on the wafer prior to acquiring the output by performing two or more inspection tests on the wafer, identifying DOI on the wafer using results of each of the two or more inspection tests separately, and combining the DOI detected using the results of each of the two or more inspection tests. In this manner, identifying the DOI may include cumulative DOI detection, which is possibly the simplest approach, in which complementary sets of DOI are detected with each inspection pass (test) and combined with a logical "OR" operation at the conclusion of all the inspection passes (tests). In another embodiment, the method includes identifying the DOI on the wafer prior to acquiring the output by performing a first inspection test on the wafer known to be capable of detecting the DOI, performing a second inspection test on the wafer known to be capable of detecting the nuisance defects, and subtracting defects detected by the second inspection test from defects detected by the first inspection test. In this manner, the method may include complementary DOI detection and nuisance detection passes in which the "defects" from a nuisance detection pass are subtracted from the "defects" of the DOI detection pass to optimize the overall S/N of the inspection.

The defects for which the output is acquired include DOI and nuisance defects. In some embodiments, the defects on the wafer are classified as DOI and nuisance defects prior to acquiring the output. The defects may be detected and classified as DOI and nuisance in a number of different manners. For example, a base recipe may be created and used to acquire output by performing one or more hot scans of the wafer. The base recipe may be set up using waferless geometry (e.g., geometry on the wafer determined for the inspection recipe without actually measuring the geometry on the wafer) and information about the design of the wafer (or design technologies) as described further herein. A "hot scan" generally refers to a scan of a wafer performed to acquire output for the wafer, which is used to detect defects on the wafer by applying relatively aggressive detection settings (e.g., thresholds substantially close to the noise floor) to the output. A set of defects of user interest may also be selected by the user or by the method using output generated by an initial hot scan. Several sampling strategies may be used to generate representative samples (potentially including diversity sampling techniques and power assisted classification (PAC) techniques, which may be performed as described further herein).

Each defect or selected defect may be classified as a DOI or as a nuisance defect (nuisance), a specific type of DOI, or a specific type of nuisance by performing defect review using an optical microscope, a scanning electron microscope (SEM), any other suitable classification tools, techniques, algorithms, methods, or some combination thereof. For example, the method may include reviewing and classifying a subset of the detected defects. In addition, if a virtual inspector (VI), which may be configured as described further herein, is directly connected to a tightly integrated review SEM, the amount of SEM data generated for the initial data set can be maximized. The review SEM may be "tightly integrated" in the sense that it has substantially the same pixel level coordinate accuracy as the inspection system. Therefore, the review SEM can be "driven" automatically to the defect sites (to position the locations of the defects in the field of view of the review SEM), and the pixels of the SEM output that correspond to the defect locations can be determined without performing defect redetection using the review SEM output. In this manner, the review SEM can be used to determine which defects detected on the wafer are nuisance and DOI. A user may also perform class mapping to indicate which classes of defects are DOI and nuisance defects as well as the relative importance of each defect type.

In one embodiment, acquiring the output includes scanning locations of the defects on the wafer using the individual optical modes. In one such embodiment, the locations of the defects on the wafer are determined with respect to an absolute reference coordinate space, and the scanning is performed based on the locations with respect to the absolute reference coordinate space. In this manner, the scanning may be performed based on relatively high coordinate accuracy versus an absolute reference such as a chip layout thereby enabling near perfect defect location accuracy from scan to scan, which may be particularly advantageous when output is to be acquired by an individual optical mode at a location of a defect but at which no defect is or can be detected by the individual optical mode. For example, when you can substantially accurately correspond pixels of output acquired during scanning of the wafer using the candidate optical modes to the previously determined defect locations, those pixels can be labeled as defective pixels regardless of whether or not a defect is detected using those pixels. Those "defective" pixels can then be used for defect detection parameter selection algorithm setup), which may be performed as described further herein. Examples of methods and systems that can be used to determine positions of defects in design data space, and therefore with respect to an absolute reference coordinate space, are described in U.S. patent application Ser. No. 11/561,735 to Kulkarni et al., which published as U.S. Patent Application Publication No. 2007/0156379 on Jul. 5, 2007, and which is incorporated by reference as if fully set forth herein. The embodiments described herein may include any step(s) of any method(s) described in this patent application, and the systems described herein may be further configured as described in this patent application. As such, the embodiments described herein can use cumulative learning about known locations of DOI and nuisance regions on a wafer enabled by relatively high coordinate accuracy versus an absolute reference. In addition, the accumulated set of points in design space may be subsequently used to label pixels from each inspection pass in image space as "pixels of interest" for defect locations or "pixels of no interest" for nuisance locations.

In some embodiments, acquiring the output includes scanning the defects on the wafer using the inspection system and storing the output produced by the scanning. For example, the method may include storing images of the entire area inspected on a VI. This storing step is optional and may be performed to avoid re-inspection and patch image grab that may be performed in other steps as described further herein. In this manner, the embodiments described herein can leverage the mass storage of images acquired by an inspection system for offline manipulation.

In another embodiment, acquiring the output includes scanning locations of the defects on the wafer using the individual optical modes and storing the output produced by scanning the locations regardless of whether or not the defects were detected at the locations using the output produced by the scanning. For example, acquiring the output as described above may include the acquisition of patch images at prescribed locations whether or not a defect is detected. As a result of such acquiring, image data for the entire original defect and nuisance "reference set" may be acquired. In this manner, the output acquired by scanning may be synthesized data. As such, the embodiments described herein may be used for deterministic multi-pass inspection recipe setup using synthesized data. In addition, as described further herein, one or more steps of the embodiments may be performed using or by a VI. In this manner, the embodiments may be used for deterministic multi-pass inspection recipe setup using synthesized data and a VI.

As described above, the output may be acquired for a set of previously detected defects. In one embodiment, the method includes identifying the defects on the wafer prior to acquiring the output by performing one or more inspection tests on the wafer, which may be performed as described herein. In one such embodiment, acquiring the output includes scanning locations of the defects on the wafer using the individual optical modes regardless of whether or not the defects were detected using results of each of the one or more inspection tests. For example, the method may include running the candidate set of inspection conditions for the final inspection recipe and acquiring patch images for detected defects as well as pseudo-defects and pseudo-nuisance, i.e., defects not detected for a given pass during the initial inspection. As a result of such acquiring, the image data for the entire original defect and nuisance "reference set" may be acquired.

In another embodiment, acquiring the output includes scanning locations of the defects on the wafer using the individual optical modes and generating difference images for the locations of the defects using output generated by the scanning and additional difference images for the locations of the defects on the wafer. In one such embodiment, the additional difference images are generated using results of one or more inspection tests performed on the wafer to identify the defects on the wafer. For example, acquiring the output may include generating pseudo-difference image patches for each of the pseudo-defect and pseudo-nuisance patch image sets from the actual difference image patches (e.g., binary defective pixel mask or a defect mask in which pixels are eliminated except for the defective pixels) captured during the initial inspection (i.e., the inspection that detected the defect location normally). For example, the difference image is essentially a defective pixel map. In this manner, the defect mask generated using the output acquired during the learning phase may be used to declare which pixels are defective in output acquired using the candidate optical modes.

In addition, the output may include reference and test (defect) images. For example, a mode used for the inspection tests may be used to generate a defect mask, and then acquiring the output may include "forcing" another mode to generate defect and reference images. Those images and the defect mask may be used to "synthesize" the difference image for the defect location. As such, the output may be synthesized in the sense that the results of normal inspection typically include the defect coordinates and three patch images (defect, reference, and difference) while the output acquired using the candidate optical modes include three patch images (defect, reference, and difference) acquired for an artificial defect location. In other words, inspection mode A may be used to detect and identify the defects on the wafer, and inspection mode B may be used to generate defect data ("pseudo-defect data") by defect synthesis.

However, the embodiments described herein may or may not include acquiring the output by scanning the wafer. For example, the embodiments described herein may include acquiring the output from an inspection system that generated the output or from a storage medium (e.g., a storage medium of the inspection system, a fab database, etc.) in which the inspection system stored the output. In another embodiment, the method includes identifying the defects on the wafer prior to acquiring the output by performing one or more inspection tests on the wafer and storing output acquired for locations on the wafer scanned during the one or more inspection tests in a storage medium, which may be performed as described herein. The storage medium may be a VI. In some such embodiments, the output of the one or more inspection tests that is stored may include only the output corresponding to defects on the wafer detected by the one or more inspection tests. Alternatively, the output of the one or more inspection tests that is stored may include the output acquired for substantially the entire wafer (i.e., all of the output acquired by the scanning performed during the one or more inspection tests). In one such embodiment, if one of the individual optical modes used for acquiring the output is used for one of the inspection test(s), acquiring the output includes retrieving the output acquired during that one inspection test from the storage medium. For example, the acquiring step may be performed offline on a VI if the intent is to use one or more of the initial inspection passes or tests for the final recipe and the whole image of the sample plan was stored on a VI for all passes during the "initial inspection," In any case, the output may be acquired in any suitable manner (e.g., by scanning the wafer using the different optical modes of the inspection system). In a similar manner, all of the output acquired using the individual optical modes may be stored in the VI thereby providing a complete set of defect data for candidate defects for each optical mode, which can then be used for additional steps described herein (e.g., tuning thresholds to increase sensitivity for each optical mode).

In another embodiment, acquiring the output includes simulating the output of the inspection system for the defects on the wafer. For example, in an automated mode of operation, to streamline the setup process further, the method may include performing simulations to generate output that would be acquired for the defects using the individual optical modes. Such simulated output may be used for the optical parameter selection stage as described further herein. The simulations may be performed using any suitable hardware and/or software such as a VI module, which may be configured to perform such simulations as described in commonly assigned U.S. patent application Ser. No. 12/234,201 by Bhaskar et al, filed Sep. 19, 2008, published on Mar. 26, 2009 as U.S. Patent Application Publication No. 2009/0080759, which is incorporated by reference as if fully set forth herein. For example, in some implementations, the embodiments may use a VI that includes a computing environment and software consistent with that of the inspection system used to acquire the images. The embodiments described herein may include any step(s) of any method(s) described in this patent application. In addition, a VI used in any of the embodiments described herein may be configured as described in this patent application.

In one embodiment, the individual optical modes for which output is acquired include all of the optical modes available on the inspection system. In this manner, each of the available individual optical modes may be evaluated as described further herein thereby ensuring that the best possible optical mode or optical mode combination is selected. However, since the number of available individual optical modes on the inspection system may number well into the tens or hundreds, some of the available optical modes may be eliminated from consideration by some method. In this manner, the output may be acquired in the methods described herein for only a portion of all available optical triodes (e.g., only the individual optical modes that have not been eliminated). One or more of the available individual optical modes may be eliminated as described in commonly assigned U.S. patent application Ser. No. 12/115, 832 by Fischer et al. filed May 6, 2008, published as U.S. Patent Application Publication No. 2008/0279444 on Nov. 13, 2008, which is incorporated by reference as if fully set forth herein. The embodiments described herein may include any step(s) of any method(s) described in this patent application.

In another embodiment, the method includes selecting the individual optical modes used to acquire the output based on a type of the inspection that will be performed on the wafer. For example, a user may perform wafer alignment and wafer layout setup steps and create a base test indicating either "array," "random," or "mixed" type inspection. "Mixed" type inspection may be inspection for both array and random areas on the wafer. In addition, the user may select a region of interest on the wafer, and the embodiments described herein may be configured to determine the type of area or areas included in the region of interest. For example, the embodiments described herein may include determining one or more characteristics of the region of interest such as periodicity or pitch of patterns in the region of interest using a technique such as pattern recognition or image analysis. In this manner, the embodiments described herein may include determining the type of inspection that will be performed on the wafer. In one such example, if the user indicates that the type of inspection is array, the individual optical modes used to acquire the output may defined by a given pixel size that is known to be appropriate or optimal for array inspection with different combinations of other optical parameters of the inspection system such as wavelengths and apertures. In addition, the individual optical modes for which output is acquired in the embodiments described herein may include best known methods (BKMs), which may be determined based on the type of inspection that will be performed on the wafer possibly in combination with any other suitable information (e.g., historical inspection results accessed in a storage medium such as a fab database). Furthermore, the initial subset of individual optical modes may be identified through optical mode elimination and/or BKMs.

The one or more combinations of the individual optical modes may include one or more combinations of two or more of the individual optical modes. For example, a combination of the individual optical modes may include two of the individual optical modes, three of the individual optical modes, four of the individual optical modes, etc. The number of optical modes included in a particular combination may be selected as described further herein. In addition, since the output that is used in the method includes output acquired for individual optical modes, many different combinations of the optical modes including different numbers of the individual optical modes may be evaluated as described further herein relatively easily and quickly.

The method also includes determining capture rates of the DOI and capture rates of the nuisance defects for the individual optical modes and for one or more combinations of the individual optical modes using the output. In this manner, the method may include determining which DOI and nuisance defects are captured and which DOI and nuisance defects are not captured by each of the individual optical modes and each of the one or more combinations. For example, in general, acquiring the output may be performed using each individual optical mode for each DOI and each nuisance. Therefore, the capture rate of the DOI for one of the individual optical modes may be determined as a function of the number of DOI that are detected using the output acquired for that individual optical mode and the total number of DOI for which the output was acquired. In one particular example, the DOI capture rate for each individual optical mode may be determined as the number of DOI detected divided by the number of DOI scanned. The capture rates of the nuisance defects may be determined for each of the individual optical modes in a similar manner. The capture rates for the combination(s) of the individual optical modes may also be determined in a similar manner.

In some embodiments, the output used for determining the capture rates includes test patch images, reference patch images, difference patch images, or some combination thereof corresponding to locations of the defects on the wafer. For example, acquiring the output may include "fabricating" reference, test, and difference image patches by applying a priori knowledge of DOI and nuisance locations. In this manner, the method may include generation of "pseudo" patch images for defect locations on the wafer. In contrast, today, one depends on the inspection system to find the defect and then give you the patch images. The embodiments described herein, however, essentially tell the inspection system where the defects are and then get information from the inspection system about these locations, which can then be used to make these locations separable as described further herein. In some sense, therefore, the normal process of inspection recipe setup is reversed to give the user or the embodiments "deterministic control" while the same or different output can be acquired for each of the defect locations.

As described above, in some embodiments, acquiring the output includes scanning locations of the defects on the wafer using the individual optical modes and generating difference images for the locations of the defects using output generated by the scanning and additional difference images for the locations of the defects on the wafer, and the additional difference images are generated using results of one or more inspection tests performed on the wafer to identify the defects on the wafer. In one such embodiment, the output used for determining the capture rates includes the difference images. Determining the capture rates using the difference images may be performed according to any embodiments described herein.

In some embodiments, the method may include assigning the pseudo-defects the appropriate manual class (e.g., nuisance or real) from the original review. In this manner, the method may include applying classifications of defects determined using one mode across other optical modes of the inspection system. In one embodiment, the method includes identifying the defects on the wafer prior to acquiring the output by performing one or more inspection tests on the wafer and storing output acquired for the defects during the one or more inspection tests in a storage medium, which may be performed as described above. In one such embodiment, determining the capture rates includes verifying the defects as the DOI and the nuisance defects by overlaying the output acquired for the defects during the one or more inspection tests and the acquiring step with output acquired for locations of the defects by defect review. For example, by coupling the embodiments described herein to a SEM, which also has pixel-level coordinate accuracy versus design, the defective pixels from original and pseudo-defects can be overlaid onto copies of the SEM images from SEM review and classification for verification that the pixels indeed indicate a DOI or nuisance defect location as the case may be. In this manner, a review SEM may be used to look at the locations of the defects identified in the inspection tests to validate what is being detected.

In one embodiment, determining the capture rates includes determining one or more characteristics of the output acquired for the defects and using the one or more characteristics to determine the capture rates. For example, the one or more characteristics of the output may include the S/N of the output corresponding to the defects. In this manner, the output acquired by the method such as data collected by the scans described above may be used to determine a descriptive metric such as a S/N metric for each defect. The S/N of the output corresponding to the defects may be determined in any suitable manner. For example, the S/N of the output corresponding to the defects may include a S/N determined by comparing the output corresponding to the defects to a reference of some sort (e.g., in a die-to-die type comparison). In one such example, the S/N may be the gray level difference between the output corresponding to the defect and the output corresponding to the reference. In this manner, the S/N of the output corresponding to the defects may be the S/N of difference images at locations in the difference images corresponding to the detects. Therefore, the S/N of the output corresponding to the defects may be a descriptive metric in that it describes the detectability of the defects. As such, the S/N may be used to determine which DOI and which nuisance are captured. In another example, the method may include extracting the normal image attributes and/or feature vectors for each pseudo-defect and pseudo-nuisance defect and using the attributes and/or feature vectors to determine the capture rates. The normal image attributes and feature vectors may include any image attributes and feature vectors known in the art and may be determined or extracted using any suitable method and/or algorithm.

In another embodiment, determining the capture rates includes determining a defect detection metric for the output acquired for the defects and using the defect detection metric to determine the capture rates. For example, the defect detection metric may include a threshold value determined by applying a defect detection algorithm to the output corresponding to the defects. The defect detection metric may therefore be a threshold metric determined for each defect. In this manner, the data collected by the scans described above or any other output acquired by the method may be used to determine a descriptive metric such as a threshold metric for each defect. One example of such a threshold metric includes brightness of the output corresponding to the defects. A higher threshold metric generally indicates that the defect is more likely to be captured. (Obviously, therefore, it is desirable for DOI to have relatively high threshold values and nuisances to have relatively low threshold values such that DOI are detected while nuisances are not.) Therefore, the defect detection metric for the output corresponding to the defects may be a descriptive metric in that it describes the detectability of the defects. As such, the defect detection metric may be used to determine which DOI and nuisance are captured. In addition, the defect detection metric that is used in the embodiments described herein may vary depending on the defect detection algorithm(s) or method(s) that will be used in the inspection (e.g., the defect detection metric may include any result of any suitable defect detection algorithm(s) or method(s) that indicates the detectability of the defects). For example, if the algorithm used to detect the defects is an MDAT algorithm, the defect detection metric may include the MDAT "Detection GL" of the "most defective" pixel within each pseudo-defect and pseudo-nuisance defect. In particular, the MDAT algorithm stores as a defect attribute the gray level offset at which the defect was detected. The most defective pixel is the first pixel detected. Therefore, the MDAT Detection GL is a measure of defectiveness and detectability. For example, the gray level offsets of the defects may be used as binning attributes, and rather than performing defect detection in a first step, the potential defects may be separated into bright and dark potential defects and then using rule-based inspection, thresholds may be collectively applied to the potential defects. In addition, the MDAT Detection GL may be used for tuning defect detection algorithms in steps described further herein.

In another embodiment, determining the capture rates includes determining one or more characteristics of the output acquired for the defects and a defect detection metric for the output acquired for the defects and using the one or more characteristics and the defect detection metric to determine the capture rates. In this manner, determining the capture rates may be achieved by considering a combination of multiple characteristics and defect detection metrics. One of such examples is the combination of S/N and a threshold metric. The combination can be arithmetic and non-arithmetic.

The method also includes determining scores for the individual optical modes and the one or more combinations as a function of the capture rates of the DOI and the capture rates of the nuisance defects. In this manner, the method includes determining an overall score per optical mode or optical mode combination. In other words, a score may be calculated for each optical mode and each optical mode combination. The overall score per mode or mode combination may be calculated as a function of DOI capture and nuisance defect (nuisance) suppression as described further herein.

In one embodiment, the scores are determined as the function of the capture rates such that the scores (1) are highest for the individual optical modes and the one or more combinations having the highest capture rates for the DOI and the lowest capture rates for the nuisance defects and (2) are lowest for the individual optical modes and the one or more combinations having the lowest capture rates for the DOI and the highest capture rates for the nuisance defects. In this manner, higher scores are given to those mode(s) and mode combination(s) that have relatively high DOI capture with relatively low nuisance capture. As such, an overall score per optical mode or optical mode combination my be utilized to measure the "goodness" of single or multiple scans. In addition, the score determined for each optical mode and optical mode combination may be a single number describing the ability of the mode or mode combination to capture DOT while suppressing nuisance. In this manner, the scores present a relatively easy way to compare the suitability of different modes and mode combinations for inspection of a wafer.

In some embodiments, the method includes determining separation between the DOI and the nuisance defects for the individual optical modes and for the one or more combinations. In addition, the method may include determining the separation between groups of DOI and nuisance defects. DOI may be grouped by design-based binning, which may be performed as described in U.S. patent application Ser. No. 11/561,659 by Zafar et al. filed Nov. 20, 2006, published as U.S. Patent Application Publication No. 2007/0288219 on Dec. 13, 2007, which is incorporated by reference as if fully set forth herein. The embodiments described herein may include any step(s) of any method(s) described in this patent application. In addition, the systems described herein may be further configured as described in this patent application. The separation between the DOI and the nuisance defects may be the separation between any one or more values that can be determined for the DOI and the nuisance defects. In addition, the one or more values corresponding to the DOI and the nuisance defects that are compared to determine the separation are preferably one or more values relating to the detectability of the DOI and the nuisance defects. In this manner, the separation between the DOI and the nuisance defects may preferably describe how well DOI and nuisance defects can be differentiated from one another. In other words, the separation between the DOI and the nuisance defects may preferably describe how well the DOI and the nuisance defects can be separated from each other in inspection results.

In one embodiment, the method includes determining one or more characteristics of the output acquired for the defects and determining separation between the DOI and the nuisance defects for the individual optical modes and for the one or more combinations using the one or more characteristics. The one or more characteristics of the output that are used to determine the separation may include any of the characteristic(s) described above and determined as described above. For example, the separation between the DOI and the nuisance defects for any mode or mode combination may be the separation between the S/N of the output corresponding to the DOI and S/N of the output corresponding to the nuisance defects.

In another embodiment, the method includes determining a defect detection metric for the output acquired for the defects and determining separation between the DOI and the nuisance defects for the individual optical modes and for the one or more combinations using the defect detection metric, which may be determined as described above. The defect detection metric for the output that is used to determine the separation may include any of the detect detection metrics described above. For example, the separation between the DOI and the nuisance defects for any mode or mode combination may be the separation between a threshold value for the output corresponding to the DOI and a threshold value for the output corresponding to the nuisance defects.

In some embodiments, the scores for the individual optical modes and the one or more combinations are determined as a function of the capture rates of the DOI and the nuisance defects and the separation between the DOI and the nuisance defects. In this manner, the overall score per optical mode or optical mode combination may be calculated as a function of DOI capture, nuisance defect suppression, and the ability of the mode or mode combination to separate DOI from nuisance groups. In addition, higher scores are given to those mode(s) that exhibit relatively high DOI capture with relatively low nuisance capture and relatively high separation. As such, the scores indicate which modes or mode combinations are most suitable for inspection of a wafer.

The scores for the individual optical modes and the one or more combinations may also be determined as a function of the capture rates for the DOI and the capture rates of the nuisance, the separation between the DOI and the nuisance, one or more characteristics of output for the DOI and the nuisance, one or more defect detection metrics for the output acquired for the DOI and the nuisance, or some combination thereof. For example, the descriptive metrics described above may be used to calculate an overall score for the individual optical modes and the one or more combinations using a function of the form:

$$\sum_{i=1}^{N} w_i d_i - \sum_{j=1}^{M} v_j n_j + A * \left[ \underset{i=1}{\overset{C_d}{\text{median}}}(T_i) - \underset{j=1}{\overset{C_n}{\text{median}}}(T_j) \right]$$

where $w_i$ is the weighting by DOI type, $d_i$ is the DOI contribution for type i, $v_j$ is the weighting by nuisance type, $n_j$ is the nuisance contribution for type j, N and M are the number of DOI and nuisance types, respectively, A is the weighting of separation importance to overall score, and T is the descriptive metric for the defects (e.g., T may be one or more characteristics of the output or one or more defect detection metrics for the output acquired for the defects). $C_d$ and $C_n$ are DOI count and nuisance count, respectively. The weightings described above may be determined in any suitable manner (e.g., based on information about different DOI types such as which DOI types are or tend to be killer defects, based on information provided by a user regarding which DOI types are most important, which types of nuisance tend to be detected relatively frequently, etc.). In addition, the above equation can be modified such that the scores are determined based on fewer variables than those shown in the equation.

The method further includes selecting one of the individual optical modes or one of the one or more combinations for the inspection of the wafer based on the scores. In one straightforward example, the scores determined for the individual optical triodes and the one or more combinations may be compared to each other, and the mode or mode combination with the highest score may be selected for use in the inspection. In addition, the scores determined as described above may be sorted in order to determine which mode or mode combination has the best performance in terms of the DOI capture and nuisance suppression.

In some embodiments, the method includes displaying the scores to a user such that the user can select one of the individual optical modes or one of the combination(s) for the inspection of the wafer. In some such embodiments, the method may include comparing the possible scores for each set of defects for each optical mode (and mode combination) and determining the maximum possible score. The maximum score per optical mode and per optical mode combination may be sorted and presented to the user such that the user can determine which mode or mode combination is "best" at finding the DOI and suppressing the nuisance while separating the DOI from the nuisance. The overall scoring system used in this step allows the user to pick an appropriate mode or set of modes quickly and easily.

The information described above may be displayed to a user in a user interface (UI). For example, the may include a table or listing that includes a number corresponding to each of the individual optical modes (i.e., a mode identity (ID), which may include a number or any other suitable mode ID) and one or more parameters that define each of the individual optical modes. The one or more parameters may include, for example, pixel size, type of illumination (e.g., normal incidence, oblique incidence, etc.), whether or not Fourier filtering, is performed for the mode, polarization polarization settings for one or more illumination channels and polarization settings for one or more detection channels), focus offset, etc., or some combination thereof.

The UI may also include another table or listing that includes the number corresponding to each of the individual optical modes, the numbers corresponding to each optical mode included in a combination, and one or more results of one or more steps of the methods described herein. For example, each row in the table or listing may correspond to one of the individual optical modes or one of the combinations. If a row corresponds to one individual optical mode, the number corresponding to that mode may be listed in the first column of the table. If a row corresponds to a combination of individual optical modes, the number of each mode included in the combination may be listed in the first columns of the row. The results may be displayed in additional columns of the table or listing. The results may include, for example, the score determined for each mode or mode combination, a descriptive metric for the DOI, a descriptive metric for the nuisance, the DOI capture rate, the nuisance capture rate, the capture rates for different types of DOI, etc., or some combination thereof.

The individual optical modes and the optical mode combinations may be arranged in the table or listing according to the scores determined for the modes and the mode combinations. For example, the mode or mode combination having the highest score may be included in the first row of the table or listing, and the mode or mode combination having the lowest score may be included in the last row of the table or listing. In this manner, the modes and mode combinations may be sorted in the table or listing in order by descending score.

The UI may include any other additional or suitable information. Such information may include information determined from the output of the inspection system or the output itself. For example, the UI may include one or more graphs that illustrate which defects were detected by different channels of an individual optical mode or a combination of individual optical modes. The UI may also include images corresponding to the defects detected on the wafer. The images may include any images that are or can be generated by an inspection or review system (e.g., patch images, difference images, SEM images, etc.).

In this manner, the UI described above may be used to display the overall score and related information to the user in a way that allows the user to quickly evaluate which mode or mode combination the user wants to select for the inspection of the wafer. For example, as described above, the UI may be configured to present the overall score in conjunction with other information that describes the capture of DOI and nuisance by each mode and mode combination. The user may also use the UI to select the mode or mode combination that the user believes produces the best inspection results and create an inspection recipe using the mode or mode combination. The inspection recipe may be generated in any suitable manner and may have any suitable format.

The embodiments described herein may also include a parameter tuning stage in which one or more defect detection parameters are selected. The one or more defect detection parameters may include any one or more parameters (e.g., one or more thresholds) for any defect detection algorithm and/or method.

In one embodiment, the method includes selecting one or more defect detection parameters for the inspection based on additional output acquired for the selected individual optical mode or the selected combination. The additional output may include any of the output described herein, which may be acquired as described herein (e.g., by scanning the wafer, by simulation, etc.). In addition, the additional output acquired for the selected mode or selected combination may be acquired for the same defects used to select the optical mode or mode combination or defects that are different than those used to select the optical mode or mode combination. For example, the additional output may include output for all of the defects detected on substantially the entire wafer using the output acquired for the selected mode or selected mode combination.

In another embodiment, if a combination of modes is selected, the method includes simultaneously selecting one or more defect detection parameters for each of the individual optical modes in the selected combination. For example, additional output including any output described further herein acquired for a selected combination of the individual optical modes may be used by the method in order to tune the defect detection parameters in a way that considers all defects from all scans simultaneously rather than one mode at a time as was performed in currently used methods. In this manner, the simultaneous sensitivity tuner allows the user or the method to achieve better sensitivity in less time than tuning each scan individually. In addition, although the defect detection parameters for each of the optical modes in the selected combination may be selected simultaneously, the defect detection parameters that are selected for each of the modes in the combination may not be the same. For example, if a selected combination includes two different optical modes, the values for the thresholds selected to be applied to the output acquired by the optical modes may be different.

In some embodiments, the method includes acquiring additional output for the selected individual optical mode or the selected combination by scanning the wafer using the selected individual optical mode or the selected combination and selecting one or more detect detection parameters for the inspection using the additional output. For example, during the parameter tuning stage, the mode or mode combination selected in the optical parameter selection stage (e.g., the best mode or mode combination determined in the optics selection stage) may be used to perform hot scan(s) of the wafer to acquire output for a sample defect set. The output acquired by the hot scan(s) may be correlated with information from previous scans (e.g., classified data), and a suitable sub-sample of the defects may be further classified. For example, the hot scan data can be classified using an optical microscope, a SEM, any other suitable classification tools, techniques, algorithms, or methods, or some combination thereof. The classified hot scan data may then be made available to the simultaneous sensitivity tuner. In this manner, once a suitable set of defects has been found and classified, and output corresponding to the defects has been acquired for each of the best mode(s) or best mode combination(s), the simultaneous sensitivity tuner allows easy optimization of the inspection recipe.

In another embodiment, the method includes simulating additional output that would be acquired for the wafer using the selected individual optical mode or the selected combination and selecting one or more defect detection parameters for the inspection using the additional output. For example, in an automated mode of operation, the methods described herein may be used to streamline the process further by using simulations to generate sufficient output for the sensitivity parameter tuning. The simulations may be performed using any suitable hardware and/or software such as a VI module, which may be configured to perform such simulations as described in the patent application by Bhaskar et al. incorporated by reference above. In addition, using the output stored in the VI, the VI may be used to alter the thresholds that are applied to the output to determine how many defects are detected with different thresholds and to tune the thresholds based on such results.

In a further embodiment, the method includes selecting one or more defect detection parameters for the inspection by acquiring additional output for the selected individual optical mode or the selected combination. The additional output may include any of the additional output described herein, which may be acquired in any manner described herein. Selecting the one or more defect detection parameters may also include detecting additional defects on the wafer using the additional output. The additional defects may be detected on the wafer as described herein or in any other suitable manner. In addition, such selection of the one or more defect detection parameters may include classifying the additional defects. The additional defects may be classified as described herein.

Furthermore, such selection of the one or more defect detection parameters may include iteratively selecting one type of the additional defects, determining one or more defect detection parameters that would prevent detection of the one type of the additional defects, and determining the additional defects that would be detected using the determined one or more defect detection parameters. As such, selecting the one or more defect detection parameters may include manipulating a defect list that includes nuisance defects, removing certain numbers or types of those defects in a certain order, determining which defect detection parameters can remove a certain defect or defects, and then calculating the effect on the defect set (e.g., to determine which defects would be detected using the new set of defect detection parameters). Determining the effect of the new defect detection parameters on the defect set or list may be performed to make sure that changing the parameters to remove certain defect(s) from the defect set or list has not adversely affected the defects that will be detected (e.g., by rendering one or more DOI no longer detectable). The method may perform iteration of this process in order to determine the best defect detection parameters that can be used to achieve the desired inspection results in terms of DOI and/or nuisance detection. For example, certain defect(s) can be selected for removal from the defect list, and the effect of changing the defect detection parameters to effect that defect removal on the defect list may be performed iteratively to optimize the DOI to nuisance capture ratio. In this manner, the method may include using information about which defects are nuisance and DOI for essentially making the defect detection algorithm do what you want. In addition, this process may be performed across all optical modes simultaneously instead of one mode at a time to make the optimization process as similar to single mode optimization as possible.

In one embodiment, the method includes automatically applying different defect detection parameters to additional output acquired using the selected mode or the selected combination based on the DOI and the nuisance defects detected using the selected mode or the selected combination and selecting one or more defect detection parameters for the selected mode or the selected combination based on results of applying the different defect detection parameters to the additional output. In this manner, the method may include looking at the available defects and/or nuisance in the selected mode or mode combination and applying algorithm parameters automatically to determine the "best" combination of the parameters. For example, the method may also or alternatively include using the additional output and/or the classified additional defects to evaluate one or more different detection parameters different values of one defect detection parameter and/or different values of a combination of defect detection parameters).

In an additional embodiment, the method includes selecting one or more defect detection parameters for the selected individual optical mode or the selected combination by determining which defects would be detected by one or more different defect detection parameters. In this manner, the method may include searching sensitivity parameters simultaneously to optimize inspection algorithm parameters given multiple or one or more optical modes. In a further embodiment, the method includes selecting one or more defect detection parameters for the selected mode or the selected combination by searching one or more different defect detection parameters simultaneously to optimize inspection results for the selected individual optical mode or the selected combination. In this manner, the method may include searching sensitivity parameters simultaneously to optimize inspection results given multiple optical modes. For example, the method may include performing a systematic search through all or a subset of combinations of defect removal options (e.g., each removal option may be defined by values for one or more defect detection parameters) to determine which DOI and/or which nuisance would be detected by each of the combinations of defect removal options. In addition, based on DOI and/or nuisance weightings, which may be supplied as part of the overall scoring process described above, a score may be determined for each of the combinations of defect removal options tested. The score may then be used to determine which set of defect detection parameters best suits the user's needs.

In some embodiments, the method includes selecting one or more defect detection parameters for the inspection by acquiring additional output for the selected individual optical mode or the selected combination. The additional output may include any of the additional output described herein and may be acquired as described herein. Selecting the one or more defect detection parameters also includes detecting additional defects using the additional output. The additional defects may be detected as described herein or in any other suitable manner. In addition, selecting the one or more defect detection parameters includes classifying the additional defects. The additional defects may be classified as described herein or in any other suitable manner. Selecting the one or more defect detection parameters further includes sorting the additional defects by classification. The additional defects may be sorted by classification as described herein or in any other suitable manner.

Furthermore, in this embodiment, selecting the one or more defect detection parameters includes displaying the sorted defects to a user such that the user can select one or more types of the additional defects. The sorted defects may be displayed to the user as described further herein. Selecting the one or more defect detection parameters in this embodiment also includes determining the one or more defect detection parameters that would prevent detection of the one or more types of the additional defects. For example, the method may include identifying defect detection parameters that can be used to remove a single defect or a single defect type from all detection channels (thereby preventing that single defect or single defect type from being detected). In this manner, the method may include allowing the user to determine which defects to remove from a sorted list containing all of the defects while the method keeps track of what parameters can be used to achieve that removal.

Selecting the one or more defect detection parameters in this embodiment also includes determining the additional defects that would be detected using the determined one or more defect detection parameters. For example, the method may include determining inspection results that would be obtained using the new defect detection parameters by determining which defects will be found and which will be missed for a given set of defect detection parameters applied to a given set of defect data. In this manner, the method may include updating the actual defect list with what is now detected and what is not based on the determined one or more defect detection parameters in order to allow for iteration until an acceptable defect list and thereby acceptable defect detection parameter set is determined.

For example, selecting the one or more defect detection parameters in this embodiment includes repeating sorting of the additional defects, displaying of the sorted defects, determining the one or more defect detection parameters, and determining the additional defects that would be detected until the user accepts the displayed defects. In this manner, the steps of defect sorting, displaying the sorted defects, receiving one or more defects or defect types selected by the user, determining the one or more defect detection parameters, and determining the defects that would be detected using the new defect detection parameters may be performed iteratively. As such, this embodiment allows the user to select one or more defects for removal, evaluate the effect of that defect removal on the inspection results (the detected defects and the non-detected defects), and determine if additional defects can or should be removed. In addition, if the effects of the defect removal on the inspection results is adverse (e.g., results in removal of a particularly important DOI type), this embodiment allows the user to select to reverse the previous defect selection (e.g., thereby putting the removed defects back in the inspection results) and perhaps select other defects for removal.

In this manner, this embodiment may include a number of steps that are performed by a user or are performed based on input from a user. For example, a user may be responsible for the sorting and/or specifying of which defects to remove. In addition, some of the steps may be performed by the user (e.g., selecting one or more types of defects to be removed), and other steps may be performed by the method (e.g., determining the defects that would be detected using the new defect detection parameters). In this manner, selecting the defect detection parameters may be performed in a user-assisted manner (e.g., with assistance from the method while allowing the user to make certain selections). The user may also be responsible for interpreting the results of each iteration and determining whether to continue with additional iterations or to accept the defect detection parameters based on the defects that will be detected and the defects that will not be detected.

As described above, the optics selection and sensitivity parameter tuning may be performed iteratively. For example, the optics selection may be performed and then sensitivity parameter tuning may be performed based on the selected optics. In addition, these steps may be performed iteratively until optical parameters and defect detection parameters that would produce acceptable, or even optimum, inspection results have been identified. Furthermore, in embodiments in which acquiring the output includes simulating the output of the inspection system that would be acquired for the defects on the wafer using the individual optical modes, and which include simulating the additional output that would be acquired for the wafer using the selected mode or the selected combination, the optics selection and the sensitivity parameter tuning may be performed iteratively. The optical parameter selection and sensitivity tuning may also be performed automatically by performing iterative tuning analysis. A variation of the overall scoring approach and detection simulation technologies described above may be applied to allow a simultaneous selection of optics mode(s) and sensitivity parameters instead of the cascaded selection described above. In this manner, the method may include selecting one or more optical parameters and one or more defect detection parameters simultaneously for one or more scans of an inspection process.

Furthermore, the "synthesized" data set described above may be used to setup an inspection recipe in a number of different manners. For example, any suitable inspection setup methods may be used on the synthesized data set to optimize the inspection for any of the candidate inspection modes. Examples of suitable inspection setup methods are described in commonly owned U.S. patent application Ser. No. 11/960,157 by Duffy et al. filed Dec. 19, 2007, published as U.S. Patent Application Publication No. 2008/0250384 on Oct. 9, 2008, which is incorporated by reference as if fully set forth herein. The embodiments described herein may include any step(s) of any method(s) described in this patent application. The systems described herein may be further configured as described in this patent application. In addition, with the "synthesized" symmetric data set, an automated regression approach to selecting the optimum imaging mode(s) and sensitivity settings may be implemented. For example, regression analysis may be performed to optimize the chance of determining the minimum number of passes to be performed during an inspection recipe where initial indications indicate that multiple passes are needed or desirable.

The optimum implementation of the embodiments described herein may be to leverage the VI to minimize the amount of time on the inspection system. For example, 100% of the detection even for the initial defect set could be performed offline. This implementation also provides a super computer that can be used for the regression analysis described above. Furthermore, if the recipe generation were performed on a VI directly connected to a tightly integrated review SEM, full verification of the inspection recipes generated by any manual or automated method could be performed efficiently. However, this concept can be generalized to any computing environment with adequate compatible resources for the image data volume and required analytical software. In addition, modifications to "power-assisted" setup tools currently implemented on some BF inspection systems that are commercially available from KLA-Tencor, Milpitas, Calif., can be modified to collect the data used to perform inspection recipe setup (e.g., one step threshold setup (OSTS)).

Each of the embodiments of the method described above may include any other step(s) of any other method(s) described herein. Furthermore, each of the embodiments of the method described above may be performed by any of the systems described herein.

Another embodiment relates to a different computer-implemented method for selecting one or more parameters for inspection of a wafer. This method includes performing one or more test inspections on a wafer to determine locations of DOI and nuisance defects on the wafer. The one or more test inspections may be performed according to any embodiments described herein. In addition, the locations of the DOI and nuisance defects on the wafer may be determined according to any embodiments described herein. The method also includes acquiring output of an inspection system at the locations on the wafer using individual optical modes of the inspection system. Acquiring the output of the inspection system at the locations on the wafer may be performed according to any of the embodiments described herein. In addition, the method includes selecting one or more parameters for the inspection of the wafer based on the output acquired at the locations on the wafer using the individual optical modes. Selecting the one or more parameters for the inspection of the wafer may be performed according to any of the embodiments described herein. The one or more parameters that are selected may include any of the parameter(s) described herein.

The embodiment of the method described above may include any other step(s) of any other method(s) described herein. Furthermore, the embodiment of the method described above may be performed by any of the systems described herein.

Figure 2:
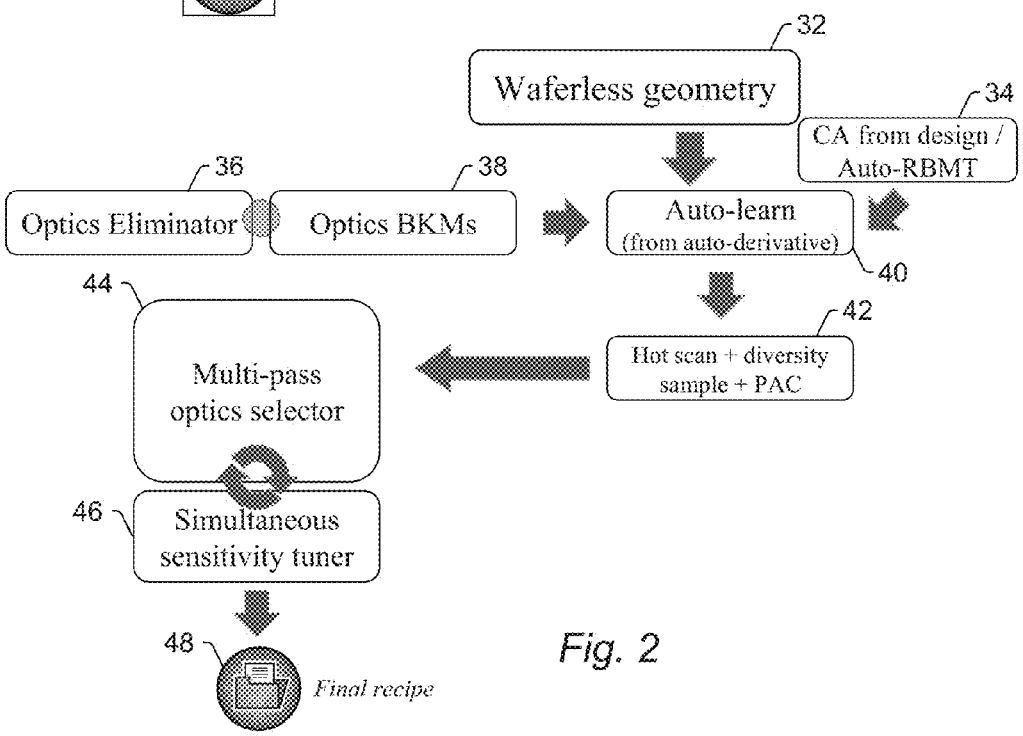

Additional embodiments of computer-implemented methods for selecting one or more parameters for inspection of a wafer are shown in FIGS. 1 and 2. It is noted that all of the steps shown in FIGS. 1 and 2 are not essential to practice of the methods shown in FIGS. 1 and 2. One or more steps may be omitted or added to the methods illustrated in FIGS. 1 and 2, and the methods can still be practiced within the scope of these embodiments.

In both methods illustrated in FIGS. 1 and 2, the functionality of the method (multi-pass optics selector and simultaneous sensitivity tuner, may be essentially the same. The difference in the two methods is how the input data is obtained (e.g., differences in method and timing for obtaining the input data).

FIG. 1 illustrates one embodiment that can be used for setting up an inspection process for one version of multi-pass inspection. This method includes two general stages in set up: multi-pass optics selector and simultaneous sensitivity tuner. This embodiment of the method may be used to set up multi-pass inspection without automation.

As shown in FIG. 1, the method may include using waferless geometry module 10 to generate a wafer layout and registration. For example, the waferless geometry module may be configured to extract geometry from mask set data for a wafer without the use of a wafer printed with a mask created from the mask set data. Therefore, the geometry is waferless in the sense that it is not acquired using a printed wafer. In addition, the geometry corresponds to information about the wafer layout and registration that can be extracted from the mask set data. The waferless geometry module may be configured to use waferless geometry to generate a wafer layout and registration as described in commonly assigned U.S. Pat. No. 7,269,816 to Bevis, which is incorporated by reference as if fully set forth herein. The embodiments described herein may include any steps of any methods described in this patent. Generating the wafer layout and registration using the waferless geometry module may be performed on-tool (i.e., on the inspection system).

As shown in FIG. 1, the method also includes using module 12 for determining settings for the care areas (CAs) using CAs determined from the design for the wafer and/or automatic region-based multi-thresholds (auto-RBMT). Module 12 may be configured to use CAs determined from the design for the wafer and/or auto-RBMT to determine settings for the CA as described in the above-referenced patent to Bevis. The settings for the CA may include any settings of the inspection system (e.g., output acquisition settings and/or defect detection settings). Determining the settings for the CA may be performed on-tool.

The method shown in FIG. 1 may include using optics eliminator module 14 and/or optics BKMs module 16 to determine the individual optical modes that will be evaluated by the method. In this manner, the individual optical modes that are evaluated by the method may include one or more BKMs and fewer than all of the optical modes available on the inspection system. For example, the optics eliminator module may determine one or more optical modes that are not suitable for inspection of the wafer and eliminate these optical mode(s) from the individual optical modes to be evaluated. As such, an initial subset of individual optical modes may be identified through the optics mode eliminator (OME) and BKMs. The optics eliminator module may be configured to eliminate one or more optical modes by performing one or more methods described in the patent application by Fischer et al. incorporated by reference above. The BKMs may be acquired by the optics BKMs module in any suitable manner using any suitable method and/or system (e.g., historical data available from a fab database) and based on any suitable information about the inspection and/or wafer (e.g., the type of inspection that will be performed on the wafer). The individual optical modes that will be evaluated the methods described herein may be generated by the optics eliminator module and/or the optics BKMs module off-tool.

A base recipe may be created in order to support collection of hot scan data (potentially using waferless geometry and setup from design technologies). For example, the wafer layout and registration, the CA settings, and the list of individual optical modes to be evaluated, all of which may be determined as described above, may be input to auto-learn (from auto-derivative) module 18 shown in FIG. 1. The method may include using the auto-learn (from auto-derivative) module to generate base recipes to collect hot scan data and optical mode data. For example, the auto-learn (from auto-derivative) module may be configured to use the wafer layout and registration, the CA settings, and the list of individual optical triodes from optics eliminator module 14 and/or optics BMWs module 16 to generate base recipes to collect hot scan data and optical mode data. In particular, the auto-learn (from auto-derivative) module may be used to generate namable inspection recipes based on information about the optical modes, information about the inspection system, and information about the wafer. The auto-learn module may be configured to perform the auto-learn functions via auto-derivative on-tool.

A set of defects of user interest may be selected from an initial hot scan (potentially using diversity sampling techniques and PAC techniques). For example, the method shown in FIG. 1 includes using the base recipes generated by module 18 to perform hot scans, diversity sampling, and PAC as shown in step 20. The hot scans may be performed as described herein or in any other suitable manner. A hot scan may be performed for each individual optical mode that is to be evaluated by the method. Several sampling strategies may be used in this step to obtain representative defect samples. For example, diversity sampling generally includes sampling multiple defects on the wafer having the greatest diversity of one or more characteristics of the multiple defects. Diversity sampling may be performed in step 20 as described in commonly assigned U.S. Pat. No. 7,570,797 to Wang et al. and commonly assigned U.S. patent application Ser. No. 11/146,342 by Dishner et al. filed Jun. 6, 2005, published as U.S. Patent Application Publication No. 2006/0287751 on Dec. 21, 2006, which are incorporated by reference as if fully set forth herein. The embodiments described herein may include any step(s) of any method(s) described in these patent applications, PAC generally includes user-assisted classification (e.g., by organizing defects by natural groupings based on features of images of the defects and then allowing the user to assign classifications to the organized defects). PAC may be performed in step 20 as described in commonly assigned U.S. Pat. No. 6,999,614 to Bakker et al. and commonly assigned U.S. patent application Ser. No. 11/249,144 by Teh et al. filed Oct. 12, 2005, published as U.S. Patent Application Publication No. 2006/0082763 on Apr. 20, 2006, which are incorporated by reference as if fully set forth herein. The embodiments described herein may include any step(s) of any method(s) described in this patent and this patent application. In addition, selected or sampled defects may be classified as a specific type using an optical microscope, a SEM, any other suitable classification tools, or some combination thereof. Furthermore, a user may provide class mapping to indicate which classes of defects are DOI and nuisance as well as the relative importance of each defect type. The hot scans, diversity sampling, and PAC performed in step 20 may, therefore, generate a classified representative sample of and nuisance data and corresponding scan data. The hot scans, the diversity sampling, and PAC may be performed on-tool.

The classified representative sample of DOI and nuisance data and corresponding scan data may be provided to multi-pass optics selector module 22. The method shown in FIG. 1 includes using multi-pass optics selector module 22 to select one of the individual optical modes or one of one or more combinations of the individual optical modes for inspection of the wafer. The multi-pass optics selector module may be configured to select a mode or mode combination according to any of the embodiments described herein. In this manner, the multi-pass optics selector module may be used to generate a best optical mode per test of the inspection process. The multi-pass optics selector module may be configured to perform the functions described above off-tool.

The best mode per test generated using multi-pass optics selector module 22 may be provided to auto-learn and bulk editor module 24. The method may include using the auto-learn and bulk editor module and the best optical mode per test generated by the multi-pass optics selector module to generate one or more updated inspection recipes. For example, the auto-learn and bulk editor module may edit inspection recipes off-line to determine if the defect detection parameters have changed and, if so, to update the defect detection parameters in the inspection recipes. The auto-learn and bulk editing functions may be performed on-tool.

The hot scans, diversity sampling, and PAC performed in step 20 may also generate a classified defect list. The classified defect list and the updated recipes generated by auto-learn and bulk editor module 24 may be provided to hot scan and diversity sample and auto-label and PAC module 26. The method may include using module 26 to acquire the additional output for the selected individual optical mode or the selected combination, detect additional defects using the additional output, and classify the additional defects, all of which may be performed as described further herein. These steps may be performed by module 26 on-tool.

In this manner, module 26 may be used to generate a representative sample of DOI and nuisance defects for the selected individual optical mode or the selected combination (or the best optical mode(s)) and corresponding scan data, which may be provided to simultaneous sensitivity tuner module 28. The best mode per test may also be provided to simultaneous sensitivity tuner module 28 by multi-pass optics selector module 22. The method may include using the simultaneous sensitivity tuner module to select one or more defect detection parameters for the inspection of the wafer (or one or more sensitivity settings per test). The simultaneous sensitivity tuner module may be configured to select the one or more defect detection parameters using the representative sample of DOI and nuisance defects for the selected individual optical mode or the selected combination, the corresponding scan data, and the best mode per test according to any of the embodiments described herein. The simultaneous sensitivity tuner module may be configured to perform the functions described above off-tool.

The method shown in FIG. 1 may then include generating final recipe 30 for the inspection of the wafer using the selected individual optical mode or the selected combination generated by multi-pass optics selector module 22 and the one or more selected defect detection parameters generated by simultaneous sensitivity tuner module 28. The generated final recipe may have any suitable format known in the art and may be stored in any suitable data structure (e.g., file, database, etc.) or storage medium known in the art.

As described above, therefore, the method shown in FIG. 1 may be performed using a number of different modules. Each of the different modules may be linked together (e.g., via one or more transmission media (not shown), which may include "wired" and/or "wireless" portions, which may serve as "data-links" between modules) to create a much easier to use set up capability. The embodiment of the method shown in FIG. 1 may include any other step(s) of any other method(s) described herein. In addition, the embodiment of the method shown in FIG. 1 may be performed by any of the systems described herein.

FIG. 2 illustrates another embodiment that can be used for multi-pass inspection set up. This embodiment automates much of the manual process that may be performed in the embodiment shown in FIG. 1. For example, the embodiment of the method shown in FIG. 2 may be used for recipe set up for multi-pass inspection with automation.

As shown in FIG. 2, the method may include using waferless geometry module 32 to generate a wafer layout and registration. Waterless geometry module 32 may be used to generate the wafer layout and registration as described further herein. In addition, waferless geometry module 32 may be configured as described herein. Generating the wafer layout and registration using waferless geometry module 32 may be performed on-tool.

As shown in FIG. 2, the method also includes using module 34 for determining settings for the CAs using the design for the wafer and/or auto-RBMT. Module 34 may be configured to determine settings for the CAs as described further herein. Module 34 may be further configured as described herein. Generating the settings for the CA using module 34 may be performed on-tool.

The method shown in FIG. 2 may include using optics eliminator module 36 and/or optics BKMs module 38 to determine the individual optical modes that will be evaluated by the method. Determining the individual optical modes that will be evaluated using optics eliminator module 36 and/or optics BKMs module 38 may be performed as described further herein. In addition, optics eliminator module 36 and optics BKMs module 38 may be further configured as described herein. The list of individual optical modes that will be evaluated may be generated by optics eliminator module 36 and optics BKMs module 38 off-tool.

The wafer layout and registration, the CA settings, and the list of individual optical modes to be evaluated may be input to auto-learn (from auto-derivative) module 40. The method may include using the auto-learn (from auto-derivative) module to generate base recipes to collect hot scan data and optical mode data as described further herein. Auto-learn (from auto-derivative) module 40 may be further configured as described herein. Auto-learn module 40 may be configured to perform the auto-learn functions via auto-derivative on-tool.

The method shown in FIG. 2 also includes using the base recipes generated by module 40 to perform hot scans, diversity sampling, and PAC as shown in step 42. The hot scans may be performed as described herein or in any other suitable manner. Diversity sampling may be performed as described herein. PAC may be performed in step 42 as described herein. The hot scans, the diversity sampling, and PAC may be performed in step 42 on-tool. The hot scans, diversity sampling, and PAC performed in step 42 may generate a classified representative sample of and nuisance data and corresponding scan data.

The classified representative sample of DOI and nuisance data and corresponding scan data may be provided to multi-pass optics selector module 44. The method shown in FIG. 2 includes using multi-pass optics selector module 44 in combination with simultaneous sensitivity tuner 46 to select one of the individual optical modes or one of one or more combinations of the individual optical modes for inspection of the wafer and to select one or more defect detection parameters for the inspection. Multi-pass optics selector module 44 and simultaneous sensitivity tuner 46 may be configured to select the mode or mode combination and the one or more defect detection parameters according to any of the embodiments described herein. In addition, the multi-pass optics selector module and the simultaneous sensitivity tuner may be configured to test optical mode and sensitivity setting options together. As such, the multi-pass optics selector module and the simultaneous sensitivity tuner may be configured to generate sensitivity and optics settings per test. The multi-pass optics selector module and the simultaneous sensitivity tuner may be configured to perform the functions described above off-tool.

The multi-pass optics selector module and the simultaneous sensitivity tuner may be configured to perform the functions described above using a VI module (not shown in FIG. 2). For example, instead of acquiring additional output for the selected individual optical mode or the selected combination of the individual optical modes by scanning the wafer, the method shown in FIG. 2 may include simulating additional output that would be acquired for the wafer using the selected individual optical mode or the selected combination of the individual optical modes and selecting the one or more defect detection parameters for the inspection using the additional output. The VI module may be configured to perform such simulations as described in the patent application by Bhaskar et al. incorporated by reference above. Using a VI module as described above allows for a combination of optics selection and sensitivity tuning for hands-off optimization.

The method shown in FIG. 2 may then include generating final recipe 48 for the inspection of the wafer using the mode or mode combination selected by multi-pass optics selector module 44 and the one or more defect detection parameters selected by simultaneous sensitivity tuner module 46. The generated final recipe may have any suitable format known in the art and may be stored in any suitable data structure (e.g., file, database, etc.) or storage medium known in the art.

As described above, therefore, the method shown in FIG. 2 may be performed using a number of different modules. Each of the different modules may be linked together as described further herein to create a much easier to use set up capability. The embodiment of the method shown in FIG. 2 may include any other step(s) of any other method(s) described herein. In addition, the embodiment of the method shown in FIG. 2 may be performed by any of the systems described herein.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method selects one of the individual optical modes or one of the one or more combinations of the individual optical modes for the inspection of the wafer, the method may include storing the selected mode or selected mode combination in an inspection recipe in a storage medium. Furthermore, the results may be stored "permanently," "semi-permanently," temporarily, or for some period of time. For example, the storage medium may be random access memory (RAM), and the results may not necessarily persist indefinitely in the storage medium.

The embodiments described herein have a number of advantages over other methods and systems for selecting one or more parameters for inspection of a wafer. For example, the embodiments described herein provide overall scoring of optical modes and optical mode combinations, which allows the user to select the right combination of optical modes for multiple scans from among the substantially large number of available combinations. In addition, the embodiments described herein help the user to determine whether multiple optical modes are needed or desirable. In particular, the embodiments allow a user to be able to explore multi-pass inspection to take full advantage of the capability of the inspection system for maximum benefits for yield control. Without the embodiments described herein, the exploration of the multi-pass space is too difficult and time consuming to conduct thereby potentially resulting in sub-optimal set ups. Once the "best" mode(s) are determined, the simultaneous sensitivity tuning steps described herein allow the user to tune the recipe as if there were only one test instead of separately having to tune the defect detection parameters n times (where n=number of individual optical modes in the inspection). Therefore, the embodiments described herein provide overall better sensitivity and nuisance suppression in less time than tuning each individual scan separately. In this manner, the embodiments described herein provide algorithm-assisted tools that can be used to allow the user to set up multi-scan inspection recipes with greatly reduced time while achieving optimum performance.

Furthermore, the embodiments described herein directly address the biggest problem that users of inspection systems have in realizing the "entitlement value" or the best theoretically achievable performance of the inspection systems. The challenge lies in converging on the optimum setup conditions in a deterministic and timely fashion. The embodiments described herein enable a much higher degree of automation in this process than is currently achievable. As such, the embodiments described herein are potentially extremely valuable.

Figure 3:
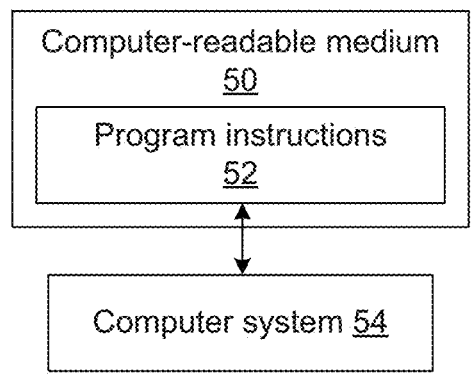
FIG. 3 is a block diagram illustrating one embodiment of a computer-readable medium that includes program instructions executable on a computer system for performing one or more of the computer-implemented methods described herein.

An additional embodiment relates to a computer-readable medium that includes program instructions executable on a computer system for performing a computer-implemented method for selecting one or more parameters for inspection of a wafer. One such embodiment is shown in FIG. 3. In particular, as shown in FIG. 3, computer-readable medium 50 includes program instructions 52 executable on computer system 54.

The computer-implemented method includes acquiring output of an inspection system for defects on the wafer using individual optical modes of the inspection system. Acquiring the output may be performed as described herein. The defects include DOI and nuisance defects. The defects may be classified as DOI and nuisance defects as described herein. The inspection system may be configured as described further herein. The method also includes determining capture rates of the DOI and capture rates of the nuisance defects for the individual optical modes and for one or more combinations of the individual optical modes using the output. Determining the capture rates may be performed as described herein. The combinations of the individual optical modes may include any of the combinations of the individual optical modes described herein. In addition, the method includes determining scores for the individual optical modes and the one or more combinations as a function of the capture rates of the DOI and the capture rates of the nuisance detects. Determining the scores may be performed as described further herein. The computer-implemented method further includes selecting one of the individual optical modes or one of the one or more combinations for the inspection of the wafer based on the scores. Selecting one of the individual optical modes or one of the one or more combinations may be performed as described further herein. The computer-implemented method for which the program instructions are executable may include any other step(s) described herein.

Program instructions 52 implementing methods such as those described herein may be stored on computer-readable medium 50. The computer-readable medium may be a storage medium such as a read-only memory, a random access memory, a magnetic or optical disk, or a magnetic tape or any other suitable computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer in system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 4:
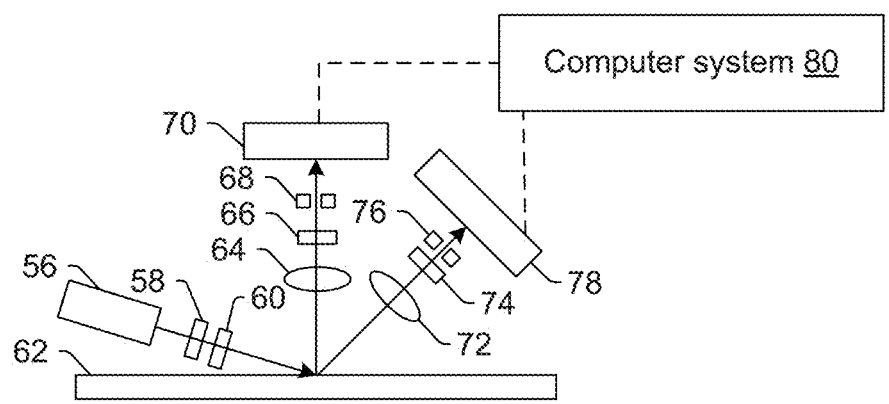
FIG. 4 is a schematic diagram illustrating a side view of one embodiment of a system configured to select one or more parameters for inspection of a wafer.

Another embodiment relates to a system configured to select one or more parameters for inspection of a wafer. One embodiment of such a system is shown in FIG. 4. The system includes an inspection system configured to acquire output for defects on the wafer using individual optical modes of the inspection system. The defects include DOI and nuisance defects. For example, as shown in FIG. 4, the inspection system includes light source 56. Light source 56 may include any suitable light source known in the art such as a laser.

The inspection system may include filter 58. As shown in FIG. 4, light source 56 may be configured to direct light to filter 58, which may be a spectral filter or any other suitable titter that can be used to alter or select the wavelength(s) of the light from light source 56 that is or are used for inspection and/or acquiring the output as described herein.

In addition, the inspection system may include more than one filter (not shown), each of which may be positioned independently in the path of the light from the light source. Each of the filters may be configured to alter the wavelength(s) of the light from the light source in a different manner. The inspection system may be configured to move the filters into and out of the path of the tight from the tight source in any suitable manner depending on which wavelength(s) of tight is or are selected for illumination of the wafer during acquisition of the output or inspection. The filter that is positioned in the path of the light from the light source during acquisition of the output or inspection may be selected as described herein.

Light from filter 58 may be directed to polarizing component 60, which may include any suitable polarizing component known in the art. In addition, the inspection system may include more than one polarizing component (not shown), each of which may be positioned independently in the path of the light from the filter. Each of the polarizing components may be configured to alter the polarization of the light from the filter in a different manner. The inspection system may be configured to move the polarizing components into and out of the path of the light from the filter in any suitable manner depending on which polarization setting is selected for illumination of the wafer during acquisition of the output or inspection. The polarization setting used for the illumination of the wafer may be selected as described herein and may include any appropriate polarization setting (e.g., p-polarized (P), s-polarized (S), and circularly polarized (C)). In addition, although the tight from light source 56 is shown in FIG. 4 to pass through filter 58 and then polarizing component 60, the light from the light source may pass through polarizing component 60 before passing through filter 58. In other words, the positions of the filter and the polarizing component in the path of the light from the light source shown in FIG. 4 may be reversed.

Light exiting polarizing component 60 is directed to wafer 62 at an oblique angle of incidence, which may include any suitable oblique angle of incidence. The inspection system may also include one or more optical components (not shown) that are configured to direct light from light source 56 to filter 58, from filter 58 to polarizing component 60, or from polarizing component 60 to wafer 62. The optical components may include any suitable optical components known in the art such as, but not limited to, a reflective optical component. In addition, the light source, the filter, the polarizing component, and optionally the one or more optical components may be configured to direct the light to the wafer at one or more angles of incidence (e.g., an oblique angle of incidence and/or a substantially normal angle of incidence). The inspection system may be configured to acquire the output described herein by scanning the light over the wafer in any suitable manner.

Light scattered from wafer 62 may be collected and detected by multiple channels of the inspection system during acquisition of the output and during inspection. For example, light scattered from wafer 62 at angles relatively close to normal may be collected by lens 64. Lens 64 may include a refractive optical element as shown in FIG. 4. In addition, lens 64 may include one or more refractive optical elements and/or one or more reflective optical elements. Light collected by lens 64 may be directed to polarizing component 66, which may include any suitable polarizing component known in the art. In addition, the inspection system may include more than one polarizing component (not shown), each of which may be positioned independently in the path of the light collected by the lens. Each of the polarizing components may be configured to alter the polarization of the light collected by the lens in a different manner. The inspection system may be configured to move the polarizing components into and out of the path of the light collected by the lens in any suitable manner depending on which polarization setting is selected for detection of the light collected by lens 64. The polarization setting used for the detection of the light collected by lens 64 may be selected as described herein and may include any suitable polarization setting (e.g., P, S, and non-polarized (N)).

Light exiting polarizing component 66 may be directed to aperture 68, which may include any suitable aperture known in the art. In addition, the inspection system may include more than one aperture (not shown), each of which may be positioned independently in the path of the light collected by the lens or exiting polarizing component 66. Each of the apertures may be configured to block a portion of the light exiting the polarizing component or the light collected by the lens in a different manner. The inspection system may be configured to move the apertures into and out of the path of the light exiting the polarizing component or the light collected by the lens in any suitable manner depending on which aperture is selected for acquisition of the output or inspection. The aperture that is positioned in the path of the light exiting polarizing component 66 or the light collected by lens 64 may be selected as described herein. In addition, although the light collected by lens 64 is shown to pass through polarizing component 66 and then aperture 68, the light collected by the lens may pass through aperture 68 before passing through polarizing component 66. In other words, the positions of the polarizing component and the aperture in the path of the light collected by lens 64 shown in FIG. 4 may be reversed.

Light exiting aperture 68 is directed to detector 70. Detector 70 may include any suitable detector known in the art such as a charge coupled device (CCD) or another type of imaging detector. Detector 70 is configured to generate output that is responsive to the scattered light collected by lens 64 and transmitted by polarizing component 66 and aperture 68 if positioned in the path of the collected scattered light. Therefore, lens 64, polarizing component 66 if positioned in the path of the light collected by lens 64, aperture 68 if positioned in the path of the light exiting polarizing component 66, and detector 70 form one channel of the inspection system. This channel of the inspection system may include any other suitable optical components (not shown) known in the art such as a spectral filter.

Light scattered from wafer 62 at different angles my be collected by lens 72. Lens 72 may be configured as described above. Light collected by lens 72 may be directed to polarizing component 74, which may include any suitable polarizing component known in the art. In addition, the inspection system may include more than one polarizing component (not shown), each of which may be positioned independently in the path of the light collected by the lens. Each of the polarizing components may be configured to alter the polarization of the light collected by the lens in a different manner. The inspection system may be configured to move the polarizing components into and out of the path of the light collected by the lens in any suitable manner depending on which polarization setting is selected for detection of the light collected by lens 72 during acquisition of the output or inspection. The polarization setting used for detection of the light collected by lens 72 may be selected as described herein and may include any suitable polarization setting P, S, and N).

Light exiting polarizing component 74 may be directed to aperture 76, which may include any suitable aperture known in the art. In addition, the inspection system may include more than one aperture not shown), each of which may be positioned independently in the path of the light collected by tens 72 or exiting polarizing component 74. Each of the apertures may be configured to block a portion of the tight exiting the polarizing component or the light collected by the lens in a different manner. The inspection system may be configured to move the apertures into and out of the path of the light exiting the polarizing component or the light collected by the lens in any suitable manner depending on which aperture is selected for acquisition of the output or inspection. The aperture that is positioned in the path of the tight exiting polarizing component 74 or the light collected by lens 72 may be selected as described herein. In addition, although the light collected by lens 72 is shown in FIG. 4 to pass through polarizing component 74 and then aperture 76, the light collected by the lens may pass through aperture 76 before passing through polarizing component 74. In other words, the positions of the polarizing component and the aperture in the path of the light collected by lens 72 shown in FIG. 4 may be reversed.

Light exiting aperture 76 is directed to detector 78, which may be configured as described above. Detector 78 is also configured to generate output that is responsive to the collected scattered light that passes through aperture 76 if positioned in the path of the scattered light. Therefore, lens 72, polarizing component 74 if positioned in the path of the light collected by lens 72, aperture 76 if positioned in the path of the light exiting polarizing component 74, and detector 78 may form another channel of the inspection system. This channel may also include any other optical components (not shown) described above. In some embodiments, lens 72 may be configured to collect light scattered from the wafer at polar angles from about 20 degrees to about 70 degrees. In addition, tens 72 may be configured as a reflective optical component (not shown) that is configured to collect light scattered from the wafer at azimuthal angles of about 360 degrees.

The inspection system shown in FIG. 4 may also include one or more other channels (not shown). For example, the inspection system may include an additional channel, which may include any of the optical components described herein such as a lens, one or more polarizing components, one or more apertures, and a detector, configured as a side channel. The lens, the one or more polarizing components, the one or more apertures, and the detector may be further configured as described herein. In one such example, the side channel may be configured to collect and detect light that is scattered out of the plane of incidence (e.g., the side channel may include a lens that is centered in a plane that is substantially perpendicular to the plane of incidence and a detector configured to detect light collected by the lens).

In another example, the inspection system may include an additional channel (not shown), which may include any of the optical components described herein such as a lens, one or more polarizing components, one or more apertures, and a detector, configured as a BF channel. The lens, the one or more polarizing components, the one or more apertures, and the detector may be further configured as described herein. In one such example, the BF channel may be configured to collect and detect light that is specularly reflected from the wafer. In another example, the system may also or alternatively be configured to illuminate the wafer at a substantially normal angle of incidence and to detect light scattered from the wafer using one or more detection channels. In this manner, the system may be configured as a normal incidence DF inspection system.

The system also includes computer system 80. Output generated by the detectors during acquisition of the output and during inspection may be provided to computer system 80. For example, the computer system may be coupled to each of the detectors (e.g., by one or more transmission media shown by the dashed lines in FIG. 4, which may include any suitable transmission media known in the art) such that the computer system may receive the output generated by the detectors. The computer system may be coupled to each of the detectors in any suitable manner.

The computer system is configured to determine capture rates of the DOI and capture rates of the nuisance detects for the individual optical modes and for one or more combinations of the individual optical modes using the output. The computer system may be configured to determine the capture rates as described herein. The computer system is also configured to determine scores for the individual optical modes and the one or more combinations as a function of the capture rates of the DOI and the capture rates of the nuisance defects. The computer system may be configured to determine the scores as described herein. In addition, the computer system is configured to select one of the individual optical modes or one of the one or more combinations for the inspection of the wafer based on the scores. The computer system may be configured to select one of the individual optical modes or one of the one or more combinations as described herein.

The computer system may be configured to perform any other step(s) of any method embodiment(s) described herein. The computer system may be further configured as described herein. The inspection system may also be further configured as described herein. Furthermore, the system may be further configured as described herein.

It is noted that FIG. 4 is provided herein to generally illustrate one configuration of an inspection system that may be included in the system embodiments described herein. Obviously, the inspection system configuration described herein may be altered to optimize the performance of the inspection system as is normally performed when designing a commercial inspection system. In addition, the systems described herein may be implemented using an existing inspection system (e.g., by adding functionality described herein to an existing inspection system) such as the Puma 9000 and 9100 series of tools that are commercially available from KLA-Tencor. For some such systems, the methods described herein may be provided as optional functionality of the system e.g., M addition to other functionality of the system). Alternatively, the system described herein may be designed "from scratch" to provide a completely new system.

In some embodiments, a system configured to perform one or more of the computer-implemented methods described herein may include an inspection system such as that described above. However, a system that is configured to perform one or more of the computer-implemented methods described herein may not include an inspection system. For example, the system may include one or more processors or one or more computer systems configured as a stand atone tool. In one such example, the system may include one or more components that are specifically designed (and optionally dedicated) to performing one or more of the computer-implemented methods described herein.

Further modifications and alternative embodiments of various aspects of the invention may be apparent to those skilled in the art in view of this description. For example, computer-implemented methods, computer-readable media, and systems for selecting one or more parameters for inspection of a wafer are provided. Accordingly, this description is to be construed as illustrative only and is for the purpose of teaching those skilled in the art the general manner of carrying out the invention, is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for selecting one or more parameters for inspection of a wafer, comprising:
    acquiring output of an inspection system for defects on the wafer using individual optical modes of the inspection system, wherein the defects comprise defects of interest and nuisance defects, wherein the inspection system comprises at least a light source and multiple channels, wherein each of the multiple channels include at least a detector, wherein the inspection system is configured to scan light from the light source over the wafer, wherein light scattered from the wafer is collected by the multiple channels and detected by the detectors in the multiple channels during acquisition of the output, and wherein the individual optical modes are defined by parameters of at least the light source and the multiple channels that are used in combination to scan the light over the wafer and to collect and detect the light scattered from the wafer to thereby acquire the output for the wafer;
    determining capture rates of the defects of interest and capture rates of the nuisance defects for the individual optical modes and for one or more combinations of the individual optical modes using the output, wherein the capture rate of the defects of interest for each of the individual optical modes and the one or more combinations is determined as a function of a number of the defects of interest detected using the output acquired using one of the individual optical modes or one of the one or more combinations and total number of the defects of interest for which the output was acquired using the one individual optical mode or combination, and wherein the capture rate of the nuisance defects for each of the individual optical modes and the one or more combinations is determined as a function of a number of the nuisance defects detected using the output acquired using the one individual optical mode or combination and total number of the nuisance defects for which the output was acquired using the one individual optical mode or combination;
    determining scores for the individual optical modes and the one or more combinations as a function of the capture rates of the defects of interest and the capture rates of the nuisance defects;
    selecting one of the individual optical modes or one of the one or more combinations for the inspection of the wafer based on the scores, wherein said determining the capture rates, said determining the scores, and said selecting are performed by a computer system, and wherein the computer system is a device having one or more processors that executes instructions from a memory medium;
    adjusting one or more of the parameters of at least one of the light source and one or more optical components of the multiple channels based on the selected one of the individual optical modes or the selected one of the one or more combinations prior to the inspection of the wafer; and
    inspecting the wafer with the inspection system having the adjusted one or more of the parameters.

2. The method of claim 1, wherein the scores are determined as the function of the capture rates such that the scores are highest for the individual optical modes and the one or more combinations having the highest capture rates for the defects of interest and the lowest capture rates for the nuisance defects and are lowest for the individual optical modes and the one or more combinations having the lowest capture rates for the defects of interest and the highest capture rates for the nuisance defects.

3. The method of claim 1, wherein said acquiring comprises scanning the defects on the wafer using the inspection system.

4. The method of claim 1, wherein said acquiring comprises scanning the defects on the wafer using the inspection system and storing the output produced by said scanning.

5. The method of claim 1, further comprising identifying the defects on the wafer prior to said acquiring by performing one or more inspection tests on the wafer, wherein said acquiring comprises scanning locations of the defects on the wafer using the individual optical modes regardless of whether or not the defects were detected using results of each of the one or more inspection tests.

6. The method of claim 1, wherein said acquiring comprises scanning locations of the defects on the wafer using the individual optical modes and storing the output produced by said scanning the locations regardless of whether or not the defects were detected at the locations using the output produced by said scanning.

7. The method of claim 1, wherein said acquiring comprises scanning locations of the defects on the wafer using the individual optical modes, wherein the locations of the defects on the wafer are determined with respect to an absolute reference coordinate space, and wherein said scanning is performed based on the locations with respect to the absolute reference coordinate space.

8. The method of claim 1, further comprising:
    identifying the defects on the wafer prior to said acquiring by performing one or more inspection tests on the wafer; and
    storing output acquired for locations on the wafer scanned during the one or more inspection tests in a storage medium,
    wherein if one of the individual optical modes used for said acquiring is used for one of the one or more inspection tests, said acquiring comprises retrieving the output acquired during the one of the one or more inspection tests from the storage medium.

9. The method of claim 1, wherein said acquiring comprises simulating the output of the inspection system for the defects on the wafer.

10. The method of claim 1, wherein said acquiring comprises scanning locations of the defects on the wafer using the individual optical modes and generating difference images for the locations of the defects using output generated by said scanning and additional difference images for the locations of the defects on the wafer, wherein the additional difference images are generated using results of one or more inspection tests performed on the wafer to identify the defects on the wafer, and wherein the output used for determining the capture rates comprises the difference images.

11. The method of claim 1, wherein the output used for determining the capture rates comprises test patch images, reference patch images, difference patch images, or some combination thereof corresponding to locations of the defects on the wafer.

12. The method of claim 1, further comprising displaying the scores to a user such that the user can select one of the individual optical modes or one of the one or more combinations for the inspection of the wafer.

13. The method of claim 1, further comprising:
identifying the defects on the wafer prior to said acquiring by performing one or more inspection tests on the wafer; and
storing output acquired for the defects during the one or more inspection tests in a storage medium,
wherein determining the capture rates comprises verifying the defects as the defects of interest and the nuisance defects by overlaying the output acquired for the defects during the one or more inspection tests and the acquiring step with output acquired for locations of the defects by defect review.

14. The method of claim 1, wherein determining the capture rates comprises determining one or more characteristics of the output acquired for the defects and using the one or more characteristics to determine the capture rates.

15. The method of claim 1, wherein determining the capture rates comprises determining a defect detection metric for the output acquired for the defects and using the defect detection metric to determine the capture rates.

16. The method of claim 1, wherein determining the capture rates comprises determining one or more characteristics of the output acquired for the defects and a defect detection metric for the output acquired for the defects and using the one or more characteristics and the defect detection metric to determine the capture rates.

17. The method of claim 1, further comprising determining one or more characteristics of the output acquired for the defects and determining separation between the defects of interest and the nuisance defects for the individual optical modes and for the one or more combinations using the one or more characteristics.

18. The method of claim 1, further comprising determining a defect detection metric for the output acquired for the defects and determining separation between the defects of interest and the nuisance defects for the individual optical modes and for the one or more combinations using the defect detection metric.

19. The method of claim 1, further comprising:
determining separation between the defects of interest and the nuisance defects for the individual optical modes and for the one or more combinations,
wherein the scores for the individual optical modes and the one or more combinations are further determined as a function of:
the capture rates of the defects of interest;
the capture rates of the nuisance defects; and
the separation between the defects of interest and the nuisance defects.

20. The method of claim 1, wherein if a combination of the individual optical modes is selected, the method further comprises simultaneously selecting one or more defect detection parameters for each of the individual optical modes in the selected combination.

21. The method of claim 1, further comprising selecting one or more defect detection parameters for the selected individual optical mode or the selected combination by determining which defects would be detected by one or more different defect detection parameters.

22. The method of claim 1, further comprising selecting one or more defect detection parameters for the selected individual optical mode or the selected combination by searching one or more different defect detection parameters simultaneously to optimize inspection results for the selected individual optical mode or the selected combination.

23. The method of claim 1, further comprising selecting one or more defect detection parameters for the inspection based on additional output acquired for the selected individual optical mode or the selected combination.

24. The method of claim 1, further comprising acquiring additional output for the selected individual optical mode or the selected combination by scanning the wafer using the selected individual optical mode or the selected combination and selecting one or more defect detection parameters for the inspection using the additional output.

25. The method of claim 1, further comprising simulating additional output that would be acquired for the wafer using the selected individual optical mode or the selected combination and selecting one or more defect detection parameters for the inspection using the additional output.

26. The method of claim 1, further comprising automatically applying different defect detection parameters to additional output acquired using the selected individual optical mode or the selected combination based on the defects of interest and the nuisance defects detected using the selected individual optical mode or the selected combination and selecting one or more defect detection parameters for the selected individual optical mode or the selected combination based on results of said applying.

27. The method of claim 1, further comprising:
selecting one or more defect detection parameters for the inspection by:
acquiring additional output for the selected individual optical mode or the selected combination;
detecting additional defects on the wafer using the additional output;
classifying the additional defects; and
iteratively:
selecting one type of the additional defects;
determining the one or more defect detection parameters that would prevent detection of the one type of the additional detects; and
determining the additional defects that would be detected using the determined one or more defect detection parameters.

28. The method of claim 1, further comprising:
selecting one or more defect detection parameters for the inspection by:
acquiring additional output for the selected individual optical mode or the selected combination;
detecting additional defects using the additional output;
classifying the additional defects;
sorting the additional defects by classification;
displaying the sorted defects to a user such that the user can select one or more types of the additional defects;

determining the one or more defect detection parameters that would prevent detection of the one or more types of the additional defects;

determining the additional defects that would be detected using the determined one or more defect detection parameters; and repeating said sorting, said displaying, said determining the one or more defect detection parameters, and said determining the additional defects that would be detected until the user accepts the displayed defects.

29. The method of claim 1, wherein the defects on the wafer are classified as defects of interest and nuisance defects prior to said acquiring.

30. The method of claim 1, further comprising identifying the defects on the wafer prior to said acquiring by performing one or more inspection tests on the wafer, wherein the one or more inspection tests do not comprise the one of the individual optical modes or the one of the one or more combinations selected for the inspection.

31. The method of claim 1, further comprising identifying the defects on the wafer prior to said acquiring by performing one or more inspection tests on the wafer, wherein the one or more inspection tests are performed using an additional inspection system having an inspection platform different than an inspection platform of the inspection system.

32. The method of claim 1, further comprising identifying the defects of interest on the wafer prior to said acquiring by performing two or more inspection tests on the wafer, identifying defects of interest on the wafer using results of each of the two or more inspection tests separately, and combining the defects of interest detected using the results of each of the two or more inspection tests.

33. The method of claim 1, further comprising identifying the defects of interest on the wafer prior to said acquiring by performing a first inspection test on the wafer known to be capable of detecting the defects of interest, performing a second inspection test on the wafer known to be capable of detecting the nuisance defects, and subtracting defects detected by the second inspection test from defects detected by the first inspection test.

34. The method of claim 1, wherein the one or more combinations comprise one or more combinations of two or more of the individual optical modes.

35. A non-transitory computer-readable medium, comprising program instructions executable on a computer system for performing a computer-implemented method for selecting one or more parameters for inspection of a wafer, wherein the computer-implemented method comprises:

acquiring output of an inspection system for defects on the wafer using individual optical modes of the inspection system, wherein the defects comprise defects of interest and nuisance defects, wherein the inspection system comprises at least a light source and multiple channels, wherein each of the multiple channels include at least a detector, wherein the inspection system is configured to scan light from the light source over the wafer, wherein light scattered from the wafer is collected by the multiple channels and detected by the detectors in the multiple channels during acquisition of the output, and wherein the individual optical modes are defined by parameters of at least the light source and the multiple channels that are used in combination to scan the light over the wafer and to collect and detect the light scattered from the wafer to thereby acquire the output for the wafer;

determining capture rates of the defects of interest and capture rates of the nuisance defects for the individual optical modes and for one or more combinations of the individual optical modes using the output, wherein the capture rate of the defects of interest for each of the individual optical modes and the one or more combinations is determined as a function of a number of the defects of interest detected using the output acquired using one of the individual optical modes or one of the one or more combinations and total number of the defects of interest for which the output was acquired using the one individual optical mode or combination, and wherein the capture rate of the nuisance defects for each of the individual optical modes and the one or more combinations is determined as a function of a number of the nuisance defects detected using the output acquired using the one individual optical mode or combination and total number of the nuisance defects for which the output was acquired using the one individual optical mode or combination;

determining scores for the individual optical modes and the one or more combinations as a function of the capture rates of the defects of interest and the capture rates of the nuisance defects;

selecting one of the individual optical modes or one of the one or more combinations for the inspection of the wafer based on the scores, wherein said determining the capture rates, said determining the scores, and said selecting are performed by the computer system, and wherein the computer system is a device having one or more processors that executes instructions from a memory medium;

adjusting one or more of the parameters of at least one of the light source and one or more optical components of the multiple channels based on the selected one of the individual optical modes or the selected one of the one or more combinations prior to the inspection of the wafer; and inspecting the wafer with the inspection system having the adjusted one or more of the parameters.

36. A system configured to select one or more parameters for inspection of a wafer, comprising:

an inspection system configured to acquire output for defects on the wafer using individual optical modes of the inspection system, wherein the defects comprise defects of interest and nuisance defects, wherein the inspection system comprises at least a light source and multiple channels, wherein each of the multiple channels include at least a detector, wherein the inspection system is further configured to scan light from the light source over the wafer, wherein light scattered from the wafer is collected by the multiple channels and detected by the detectors in the multiple channels during acquisition of the output, and wherein the individual optical modes are defined by parameters of at least the light source and the multiple channels that are used in combination to scan the light over the wafer and to collect and detect the light scattered from the wafer to thereby acquire the output for the wafer; and a computer system configured to:

determine capture rates of the defects of interest and capture rates of the nuisance defects for the individual optical modes and for one or more combinations of the individual optical modes using the output, wherein the capture rate of the defects of interest for each of the individual optical modes and the one or more combinations is determined as a function of a number of the defects of interest detected using the output acquired using one of the individual optical modes or one of the one or more combinations and total number of the defects of interest for which the output was acquired using the one individual optical mode or combination, and wherein the capture rate of the nuisance detects for each of the individual optical modes and the one or more combinations is determined as a function of a number of the nuisance defects detected using the output acquired using the one individual optical mode or combination and total number of the nuisance defects for which the output was acquired using the one individual optical mode or combination;

determine scores for the individual optical modes and the one or more combinations as a function of the capture rates of the defects of interest and the capture rates of the nuisance defects;

select one of the individual optical modes or one of the one or more combinations for the inspection of the wafer based on the scores, wherein the computer system is a device having one or more processors that executes instructions from a memory medium; and adjust one or more of the parameters of at least one of the light source and one or more optical components of the multiple channels based on the selected one of the individual optical modes or the selected one of the one or more combinations prior to the inspection of the wafer;

wherein the inspection system is further configured to inspect the wafer while having the adjusted one or more of the parameters.

37. The system of claim 36, wherein the scores are determined as the function of the capture rates such that the scores are highest for the individual optical modes and the one or more combinations having the highest capture rates for the defects of interest and the lowest capture rates for the nuisance defects and are lowest for the individual optical modes and the one or more combinations having the lowest capture rates for the defects of interest and the highest capture rates for the nuisance defects.

38. The system of claim 36, wherein said acquisition of the output comprises scanning the defects on the wafer using the inspection system.

39. The system of claim 36, wherein said acquisition of the output comprises scanning the defects on the wafer using the inspection system and storing the output produced by said scanning.

40. The system of claim 36, wherein the computer system is further configured for identifying the defects on the wafer prior to said acquisition of the output by performing one or more inspection tests on the wafer with the inspection system, and wherein said acquisition of the output comprises scanning locations of the defects on the wafer using the individual optical modes regardless of whether or not the defects were detected using results of each of the one or more inspection tests.

41. The system of claim 36, wherein said acquisition of the output comprises scanning locations of the defects on the wafer using the individual optical modes and storing the output produced by said scanning the locations regardless of whether or not the defects were detected at the locations using the output produced by said scanning.

42. The system of claim 36, wherein said acquisition of the output comprises scanning locations of the defects on the wafer using the individual optical modes, wherein the locations of the defects on the wafer are determined with respect to an absolute reference coordinate space, and wherein said scanning is performed based on the locations with respect to the absolute reference coordinate space.

43. The system of claim 36, wherein the computer system is further configured for:

identifying the defects on the wafer prior to said acquisition of the output by performing one or more inspection tests on the wafer; and storing output acquired for locations on the wafer scanned during the one or more inspection tests in a storage medium, wherein if one of the individual optical modes used for said acquisition of the output is used for one of the one or more inspection tests, said acquisition of the output comprises retrieving the output acquired during the one of the one or more inspection tests from the storage medium.

44. The system of claim 36, wherein said acquisition of the output comprises simulating the output of the inspection system for the defects on the wafer.

45. The system of claim 36, wherein said acquisition of the output comprises scanning locations of the defects on the wafer using the individual optical modes and generating difference images for the locations of the defects using output generated by said scanning and additional difference images for the locations of the defects on the wafer, wherein the additional difference images are generated using results of one or more inspection tests performed on the wafer to identify the defects on the wafer, and wherein the output used for determining the capture rates comprises the difference images.

46. The system of claim 36, wherein the output used to determine the capture rates comprises test patch images, reference patch images, difference patch images, or some combination thereof corresponding to locations of the defects on the wafer.

47. The system of claim 36, wherein the computer system is further configured for displaying the scores to a user such that the user can select one of the individual optical modes or one of the one or more combinations for the inspection of the wafer.

48. The system of claim 36, wherein the computer system is further configured for:

identifying the defects on the wafer prior to said acquisition of the output by performing one or more inspection tests on the wafer; and storing output acquired for the defects during the one or more inspection tests in a storage medium, wherein the computer system is further configured to determine the capture rates by verifying the defects as the defects of interest and the nuisance defects by overlaying the output acquired for the defects during the one or more inspection tests and said acquisition of the output with output acquired for locations of the defects by defect review.

49. The system of claim 36, wherein the computer system is further configured to determine the capture rates by determining one or more characteristics of the output acquired for the defects and using the one or more characteristics to determine the capture rates.

50. The system of claim 36, wherein the computer system is further configured to determine the capture rates by determining a defect detection metric for the output acquired for the defects and using the defect detection metric to determine the capture rates.

51. The system of claim 36, wherein the computer system is further configured to determine the capture rates by determining one or more characteristics of the output acquired for the defects and a defect detection metric for the output acquired for the defects and using the one or more characteristics and the defect detection metric to determine the capture rates.

52. The system of claim 36, wherein the computer system is further configured for determining one or more characteristics of the output acquired for the defects and determining separation between the defects of interest and the nuisance defects for the individual optical modes and for the one or more combinations using the one or more characteristics.

53. The system of claim 36, wherein the computer system is further configured for determining a defect detection metric for the output acquired for the defects and determining separation between the defects of interest and the nuisance defects for the individual optical modes and for the one or more combinations using the defect detection metric.

54. The system of claim 36, wherein the computer system is further configured for:
determining separation between the defects of interest and the nuisance defects for the individual optical modes and for the one or more combinations,
wherein the scores for the individual optical modes and the one or more combinations are further determined as a function of:
the capture rates of the defects of interest;
the capture rates of the nuisance defects; and
the separation between the defects of interest and the nuisance defects.

55. The system of claim 36, wherein if a combination of the individual optical modes is selected, the computer system is further configured for simultaneously selecting one or more defect detection parameters for each of the individual optical modes in the selected combination.

56. The system of claim 36, wherein the computer system is further configured for selecting one or more defect detection parameters for the selected individual optical mode or the selected combination by determining which detects would be detected by one or more different defect detection parameters.

57. The system of claim 36, wherein the computer system is further configured for selecting one or more defect detection parameters for the selected individual optical mode or the selected combination by searching one or more different defect detection parameters simultaneously to optimize inspection results for the selected individual optical mode or the selected combination.

58. The system of claim 36, wherein the computer system is further configured for selecting one or more defect detection parameters for the inspection based on additional output acquired for the selected individual optical mode or the selected combination.

59. The system of claim 36, wherein the inspection system is further configured for acquiring additional output for the selected individual optical mode or the selected combination by scanning the wafer using the selected individual optical mode or the selected combination, and wherein the computer system is further configured for selecting one or more defect detection parameters for the inspection using the additional output.

60. The system of claim 36, wherein the computer system is further configured for simulating additional output that would be acquired for the wafer using the selected individual optical mode or the selected combination and selecting one or more defect detection parameters for the inspection using the additional output.

61. The system of claim 36, wherein the computer system is further configured for automatically applying different defect detection parameters to additional output acquired using the selected individual optical mode or the selected combination based on the defects of interest and the nuisance defects detected using the selected individual optical mode or the selected combination and selecting one or more defect detection parameters for the selected individual optical mode or the selected combination based on results of said applying.

62. The system of claim 36, wherein the computer system is further configured for:
selecting one or more defect detection parameters for the inspection by:
acquiring additional output for the selected individual optical mode or the selected combination;
detecting additional detects on the wafer using the additional output;
classifying the additional defects; and
iteratively:
selecting one type of the additional defects;
determining the one or more defect detection parameters that would prevent detection of the one type of the additional defects; and
determining the additional defects that would be detected using the determined one or more defect detection parameters.

63. The system of claim 36, wherein the computer system is further configured for:
selecting one or more defect detection parameters for the inspection by:
acquiring additional output for the selected individual optical mode or the selected combination;
detecting additional defects using the additional output;
classifying the additional defects;
sorting the additional detects by classification;
displaying the sorted defects to a user such that the user can select one or more types of the additional defects;
determining the one or more defect detection parameters that would prevent detection of the one or more types of the additional defects;
determining the additional defects that would be detected using the determined one or more defect detection parameters; and
repeating said sorting, said displaying, said determining the one or more defect detection parameters, and said determining the additional defects that would be detected until the user accepts the displayed defects.

64. The system of claim 36, wherein the defects on the wafer are classified as defects of interest and nuisance defects prior to said acquisition of the output.

65. The system of claim 36, wherein the computer system is further configured for identifying the defects on the wafer prior to said acquisition of the output by performing one or more inspection tests on the wafer, and wherein the one or more inspection tests do not comprise the one of the individual optical modes or the one of the one or more combinations selected for the inspection.

66. The system of claim 36, wherein the computer system is further configured for identifying the defects on the wafer prior to said acquisition of the output by performing one or more inspection tests on the wafer, and wherein the one or more inspection tests are performed using an additional inspection system having an inspection platform different than an inspection platform of the inspection system.

67. The system of claim 36, wherein the computer system is further configured for identifying the defects of interest on the wafer prior to said acquisition of the output by performing two or more inspection tests on the wafer, identifying defects of interest on the wafer using results of each of the two or more inspection tests separately, and combining the defects of interest detected using the results of each of the two or more inspection tests.

68. The system of claim 36, wherein the computer system is further configured for identifying the defects of interest on the wafer prior to said acquisition of the output by performing a first inspection test on the wafer known to be capable of detecting the defects of interest, performing a second inspection test on the wafer known to be capable of detecting the nuisance defects, and subtracting defects detected by the second inspection test from defects detected by the first inspection test.

69. The system of claim 36, wherein the one or more combinations comprise one or more combinations of two or more of the individual optical modes.

* * * * *